United States Patent
Peel et al.

(10) Patent No.: US 9,724,389 B2
(45) Date of Patent: Aug. 8, 2017

(54) SYSTEM AND METHOD FOR MULTIPHASIC RELEASE OF GROWTH FACTORS

(71) Applicant: INDUCE BIOLOGICS, INC., Toronto (CA)

(72) Inventors: Sean A. F. Peel, Oakville (CA); Cameron M. L. Clokie, Toronto (CA)

(73) Assignee: INDUCE BIOLOGICS, INC., Toronto, CA (US)

(*) Notice: Subject to any disclaimer, the term of this patent is extended or adjusted under 35 U.S.C. 154(b) by 0 days.

(21) Appl. No.: 14/509,840

(22) Filed: Oct. 8, 2014

(65) Prior Publication Data
US 2015/0196620 A1    Jul. 16, 2015

Related U.S. Application Data

(63) Continuation of application No. PCT/CA2012/050738, filed on Oct. 17, 2012, which
(Continued)

(51) Int. Cl.
*A61K 38/18* (2006.01)
*A61K 47/02* (2006.01)
(Continued)

(52) U.S. Cl.
CPC ........ *A61K 38/1875* (2013.01); *A61K 9/0024* (2013.01); *A61K 9/1611* (2013.01);
(Continued)

(58) Field of Classification Search
None
See application file for complete search history.

(56) References Cited

U.S. PATENT DOCUMENTS

| 4,761,471 A | 8/1988 | Urist | 530/350 |
| 4,789,732 A | 12/1988 | Urist | 530/350 |

(Continued)

FOREIGN PATENT DOCUMENTS

| WO | WO 02/070029 | 9/2002 | A61L 27/12 |
| WO | WO 2006/093808 | 9/2006 | A61K 38/00 |

(Continued)

OTHER PUBLICATIONS

Chen, F. et al., "Research progress of growth factor carrier and sustained-release system" *Journal of International Medicine: Stomatology* 32(1): 44-46 (Jan. 31, 2005).
(Continued)

*Primary Examiner* — Xiaozhen Xie
(74) *Attorney, Agent, or Firm* — J. Peter Paredes; David G. Rosenbaum; Rosenbaum IP, P.C.

(57) ABSTRACT

A system for multiphasic delivery of at least one growth factor at a treatment site comprises a delivery vehicle for releasing at least one growth factor in an initial release profile and a carrier for releasing at least one growth factor in a sustained release profile. The initial release profile releases at least one growth factor over a period of hours to days, wherein the growth factor is released in a large amount initially, with the remainder being released in progressively lower amounts. The sustained release profile releases at least one growth factor over a period of days to weeks, wherein the growth factor is released at a generally constant amount over such period. The system of the invention is particularly suited for applications on bioimplants. The invention also comprises methods and kits for multiphasic delivery of at least one growth factor. The invention also comprises calcium sulphate as a carrier for releasing at least one growth factor in both single and multiphasic systems for delivering at least one growth factor at a treatment site.

14 Claims, 10 Drawing Sheets

Related U.S. Application Data is a continuation-in-part of application No. PCT/CA2012/050234, filed on Apr. 11, 2012.

(60) Provisional application No. 61/474,049, filed on Apr. 11, 2011.

(51) Int. Cl.

| | | |
|---|---|---|
| *A61K 47/10* | (2017.01) | |
| *A61K 47/34* | (2017.01) | |
| *A61K 9/52* | (2006.01) | |
| *A61K 9/54* | (2006.01) | |
| *A61L 27/54* | (2006.01) | |
| *A61K 9/50* | (2006.01) | |
| *A61K 9/00* | (2006.01) | |
| *A61K 9/16* | (2006.01) | |
| *A61L 27/46* | (2006.01) | |
| *A61K 47/48* | (2006.01) | |
| *A61K 9/19* | (2006.01) | |

(52) U.S. Cl.
CPC .......... *A61K 9/1641* (2013.01); *A61K 9/1682* (2013.01); *A61K 9/19* (2013.01); *A61K 9/5084* (2013.01); *A61K 38/18* (2013.01); *A61K 38/1825* (2013.01); *A61K 38/1841* (2013.01); *A61K 38/1858* (2013.01); *A61K 38/1866* (2013.01); *A61K 47/02* (2013.01); *A61K 47/10* (2013.01); *A61K 47/34* (2013.01); *A61K 47/48861* (2013.01); *A61L 27/46* (2013.01); *A61L 27/54* (2013.01)

(56) References Cited

U.S. PATENT DOCUMENTS

| | | | | |
|---|---|---|---|---|
| 4,795,804 | A | 1/1989 | Urist | 530/350 |
| 4,857,456 | A | 8/1989 | Urist | 435/7 |
| 4,877,864 | A | 10/1989 | Wang et al. | 530/324 |
| 5,013,649 | A | 5/1991 | Wang et al. | 435/69.1 |
| 5,166,058 | A | 11/1992 | Wang et al. | 435/69.1 |
| 5,385,887 | A | 1/1995 | Yim et al. | 514/12 |
| 5,618,924 | A | 4/1997 | Wang et al. | 530/399 |
| 5,631,142 | A | 5/1997 | Wang et al. | 435/69.1 |
| 6,150,328 | A | 11/2000 | Wang et al. | 514/12 |
| 6,503,109 | B1 | 1/2003 | Duffield et al. | 440/51 |
| 6,589,549 | B2 | 7/2003 | Shih et al. | 424/426 |
| 6,593,109 | B1 | 7/2003 | Israel et al. | 435/69.1 |
| 6,998,128 | B2 | 2/2006 | Haggard et al. | 424/400 |
| 2002/0015737 | A1* | 2/2002 | Shih | A61K 9/143 424/499 |
| 2006/0257488 | A1* | 11/2006 | Hubbard | A61K 9/0024 424/486 |
| 2006/0257492 | A1 | 11/2006 | Wen et al. | 424/489 |
| 2007/0190102 | A1 | 8/2007 | Luo | 424/423 |
| 2007/0248675 | A1 | 10/2007 | Tae et al. | 424/486 |
| 2007/0255422 | A1 | 11/2007 | Wei et al. | 623/23.51 |
| 2008/0233165 | A1* | 9/2008 | Alexander | A61L 27/025 424/423 |
| 2010/0021518 | A1 | 1/2010 | Scifert | 424/423 |
| 2011/0182911 | A1 | 7/2011 | Clokie et al. | 424/158.1 |
| 2011/0208305 | A1 | 8/2011 | Malinin et al. | 623/13.14 |

FOREIGN PATENT DOCUMENTS

| | | | |
|---|---|---|---|
| WO | WO 2010/000061 | 1/2010 | A61L 27/54 |
| WO | WO 2011/016881 | 2/2011 | A61K 9/50 |

OTHER PUBLICATIONS

Chinese Search Report issued in a corresponding foreign application, pp. 1-5 (Dec. 17, 2014).

Chinese Search Report issued in a corresponding foreign application, pp. 1-4 (Nov. 4, 2015).

Hu, Rongfeng, "Industry Pharmaceuticas, 1st Edition" pp. 436-437 (Aug. 31, 2010).

International Search Report issued in a corresponding foreign application; pp. 1-4 (Aug. 8, 2012).

Japanese Search Report issued in a corresponding foreign application, pp. 1-6 (Jan. 25, 2016).

Johnston, T.P., et al., "Sustained delivery of Interlukin-2 from a poloxamer 407 gel matrix following intraperitoneal injection in mice" *Pharmaceutical Research* 9(3): 425-434 (1992).

Zhou, J., et al., "An evaluation of hydroxyapatite and biphasic calcium and phosphaste in combination with pluronic F127 and BMP on bone repair" *Craniofac Surg*. 18(6): 1264-1275 (2007).

Aberg, et al., "Calcium sulfate spinal cord scaffold: A study on degradation and fibroblast growth factor 1 loading and release" *Journal of Biomaterials Applications*, 26: 667-685 (2012).

Azari, et al., "Therapeutic potential of bone morphogenetic proteins" *Expert Opin Invest Drugs* 10(9): 1677-1686 (2001).

Barr, et al., "Comparison of the osteoinductivity of bioimplants containing recombinant human bone morphogenetic proteins 2 (infuse) and 7 (OP-1)" *Oral Surg Oral Med Oral Pathol Oral Radiol Endod*. 109(4): 531-540 (2010).

Boden, "The ABCs of BMPs" *Orthopaedic Nursing* 24(1): 49-52 (2005).

Chen et al., "Effects of Chitosan-coated pressed calcium sulfate pellets combined with recombinant human bone morphogenetic protein 2 on bone formation in femoral condyle-contained bone defects" *J. Craniofacial Surg*., 21(1): 188-197 (2010).

Clokie & Bell, "Recombinant human transforming growth factor β-1 and its effects on osseointegration" *J. Craniofacial Surg*. 14(3): 268-277 (2003).

Clokie and Urist, "Bone morphogenetic proteins excipients: Comparative observations on poloxamer" *Plast. Reconstr. Surg*. 105(2): 628-637 (2000).

Damien, C., et al., "Student research award in the graduate degree candidate category, 16th annual meeting of the society for biomaterials, Charleston, S.C., Investigation of a hydroxyapatite and calcium sulfate composite supplemented with an osteoinductive factor" *J. Biomed. Mat. Res*., 24: 639-654 (1990).

Damien, C., et al., "Purified bovine BMP extract and collagen for spine arthrodesis" *Spine* 27(16S): S50-S58 (2002).

Friess, et. al., "Characterization of absorbable collagen sponges as rhBMP-2 carriers" *Intl. J. Pharm*.,187: 91-99 (1999).

Gore, ed., "Spectrophotometry and spectrofluorimetry: A practical approach" *Oxford University Press*, 2000.

Gosling, ed., "Immunoassays: A practical approach" *Oxford University Press*. (2000).

Harlow and Lane, "Using Antibodies: A Laboratory Manual" *Cold Spring Harbor Laboratory Press*. (1999).

Hockfield, et al., "Selected methods for antibody and nucleic acid probes" *Cold Spring Harbor Laboratory Press* (1993).

Hoffman, et al., "Perspectives in the biological function, the technical and therapeutic application of bone morphogenetic proteins" *Appl. Microbiol. Biotech* 57: 294-308 (2001).

Hollinger, et al., "Recombinant human platelet-derived growth factor: Biology and clinical applications" *JBJS* 90(Suppl): 48-54 (2008).

http://www.osteohealth.com/GEM21S.aspx (2015).

Hu, et al., "The osteoinductive activity of bone morphogenetic protein (BMP) purified by repeated extracts of bovine bone" *Growth Factors*, 22(1): 29-33 (2004).

Humber, et al., "Oral and maxillofacial implants. Bone healing with an in situ-formed bioresorbable polyethylene glycol hydrogel membrane in rabbit calvarial defects" *Oral Surg. Oral Med Oral Pathol. Oral Radiol. Endod*. 109(3): 372-384 (2010).

International Search Report issued in corresponding foreign application, PCT/CA2012/050738, pp: 1-6 (Oct. 17, 2013).

Kawaguchi, et al., "Local application of recombinant human fibroblast growth factor-2 on bone repair: A dose-escalation prospective trial on patients with osteotomy" *J. Orthopaedic Res*. 25(4): 480-487 (2007).

(56) References Cited

OTHER PUBLICATIONS

Kawai and Urist, "Quantitative computation of induced heterotopic bone formation by an image analysis system" *Clin. Orthop. Relat. Res.*, 233: 262-267 (1988).

Kirsch, et al., "BMP-2 antagonists emerge from alterations in the low-affinity binding epitope for receptor BMPR-II" *EMBO J* 19(13): 3314-3324 (2000).

Meyer, et al., "Gene expression in older rats with delayed union of femoral fractures" *J Bone Jt. Surg* 85-A(7): 1243-1254 (2003).

Millner, ed., "High Resolution Chromatography: A Practical Approach" *Oxford University Press* (1999).

Oliver, ed., "HPLC of Macromolecules: A Practical Approach" *Oxford University Press* (1998).

Parsons, J., et al., "Osteoconductive composite grouts for orthopedic use" Annals N.Y. Acad. Sci., 523:190-207 (1988).

Peel, et al., In search of the ideal bone morphogenetic protein delivery system: In vitro studies on demineralized bone matrix, purified, and recombinant bone morphogenetic protein: *J Craniofacial Surg.* 14(3): 284-291 (2003).

Rasubala, et al., "Platelet derived growth factor and bone morphogenetic protein in the healing in mandibular fractures in rats" *British Journal of Oral and Maxillofacial Surgery* 41: 173-178 (2003).

Ruppert, et al., "Human bone morphogenetic protein 2 contains a heparin-binding site which modifies its biological activity" *Eur J Biochem* 237: 295-302 (1996).

Steinmuller-Nethl, D. et al., "Strong binding of bioactive BMP-2 to nanocrystalline diamond by physisorption" *Biomaterials*, 27: 4547-4556 (2006).

Street, et al., "Vascular endothelial growth factor stimulates bone repair by promoting angiogenesis and bone turnover" *PNAS* 99(15): 9656-9661 (2002).

Szpalski, et al., "Bony engineering using time-release porous scaffolds to provide sustained growth factor delivery" *The Journal of Carniofacial Surgery* 23(3): 638-644 (2012).

Tyndall, et al., "Decreased platelet derived growth factor expression during fracture healing in diabetic animals" *Clinical Orthopedics and Related Research* 408: 319-330 (2003).

Uludag, et al., "Characterization of rhBMP-2 pharmacokinetics implanted with biomaterial carriers in the rat ectopic model" *J Biomed Mater Res* 46: 193-202 (1999).

Vallejo, et al., "Renaturation and purification of bone morphogenetic protein-2 produced as inclusion bodies in high-cell-density cultures of recombinant *Escherichia coli*" *J Biotech* 94:185-194 (2002).

Wang, et al., "Recombinant human bone morphogenetic protein induces bone formation" *Proc Natl Acad Sci USA* 87: 2220-2224 (1990).

Winn, et al., "Sustained release emphasizing recombinant human bone morphogenetic protein-2" *Adv. Drug Del. Rev.* 31: 303-318 (1998).

Yeh, et al., "Cartilage-derived morphogenetic proteins induce osteogenic gene expression in the C2C12 mesenchymal cell line" *J Cellular Biochem.* 95: 173-188 (2005).

\* cited by examiner

SYSTEM AND METHOD FOR MULTIPHASIC RELEASE OF GROWTH FACTORS

CROSS REFERENCE TO PRIOR APPLICATIONS

This application is a continuation of PCT/CA2012/050738, filed Oct. 17, 2012, which is a continuation-in-part application of PCT/CA2012/050234, filed on Apr. 11, 2012, which claims priority under the Paris Convention from U.S. Provisional Application No. 61/474,049, filed on Apr. 11, 2011, the entire contents of each application are incorporated herein by reference.

FIELD OF THE INVENTION

This invention relates to systems and methods for releasing biological substances. In particular, the invention relates to the release of growth factors associated with bioimplants. More particularly, the invention provides a system and method for producing a multiphasic release profile of at least one growth factor to improve the performance of the bioimplant.

BACKGROUND OF THE INVENTION

Growth factors (GFs) are peptides and proteins that stimulate the growth and/or differentiation of cells via the interaction of the GFs with specific cell surface receptors. Growth factors play an integral role in the repair and regeneration of tissues and exogenous application of GFs can be used to stimulate the repair of various tissues and organs including bone, cartilage, skin and mucosa and to enhance repair of tissues through the stimulation of angiogenesis at the repair site.

The transforming growth factor beta (TGFβ) superfamily of secreted growth and differentiation factors in mammals has over 30 members. These dimeric proteins are characterized by a conserved seven cystine knot-based structure. They regulate the proliferation, differentiation and migration of many cell types, and have important roles in morphogenesis, organogenesis, tissue maintenance and wound healing. The TGFβ superfamily of growth factors can be subdivided into several subfamilies including the transforming growth factor beta subfamily, the bone morphogenetic protein (BMP) and growth and differentiation factor (GDF) family (also called the BMP subfamily), and the inhibin and activin subfamily.

The BMP subfamily of the TGFβ superfamily comprises at least twenty proteins, including BMP-2, BMP-3 (also known as osteogenin), BMP-3b (also known as growth and differentiation factor 10, GDF-10), BMP-4, BMP-5, BMP-6, BMP-7 (also known as osteogenic protein-1, OP-1), BMP-8 (also known as osteogenic protein-2, OP-2), BMP-9, BMP-10, BMP-11 (also known as growth and differentiation factor 8, GDF-8, or myostatin), BMP-12 (also known as growth and differentiation factor 7, GDF-7), BMP-13 (also known as growth and differentiation factor 6, GDF-6), BMP-14 (also known as growth and differentiation factor 5, GDF-5), and BMP-15 (for a review, see e.g., Azari et al. Expert Opin Invest Drugs 2001; 10:1677-1686).

BMPs have been shown to stimulate matrix synthesis in chondroblasts; stimulate alkaline phosphatase activity and collagen synthesis in osteoblasts, induce the differentiation of early mesenchymal progenitors into osteogenic cells (osteoinduction), regulate chemotaxis of monocytes and mesenchymal cells, and regulate the differentiation of neural cells (for a review, see e.g., Azari et al. Expert Opin Invest Drugs 2001; 10:1677-1686 and Hoffman et al. Appl. Microbiol. Biotech 2001; 57:294-308).

One of the many functions of BMP proteins is to induce cartilage, bone, and connective tissue formation in vertebrates. The most osteoinductive members of the BMP subfamily are BMP-2, BMP-4, BMP-6, BMP-7, BMP-8 and BMP-9 (see, e.g., Hoffman et al., Appl. Microbiol Biotech 2001, 57:294-308; Yeh et al., J Cellular Biochem., 2005; 95:173-188; and Boden, Orthopaedic Nursing 2005, 24:49-52). This osteoinductive capacity of BMPs has long been considered very promising for a variety of therapeutic and clinical applications, including fracture repair; spine fusion; treatment of skeletal diseases, regeneration of skull, mandibular, and bone defects; and in oral and dental applications such as dentogenesis and cementogenesis during regeneration of periodontal wounds, extraction socket grafting, alveolar ridge augmentation, and sinus augmentation. Currently, recombinant human BMP-2 sold as INFUSE® by Medtronic FDA approved for use in spinal fusion surgery, for repair of fracture non-unions and for use in oral surgery, while and recombinant human BMP-7 sold as OP-1@ by Stryker is approved as an alternative to autograft in recalcitrant long bone nonunion and for revision posterolateral (intertransverse) lumbar spine fusions, where autograft and bone marrow harvest are not feasible or are not expected to promote fusion.

Other recombinant growth factors that have been used exogenously to enhance bone repair include various TGFβs (see Clokie & Bell, J. Craniofacial Surg. 2003, 14:268-77), members of the fibroblast growth factor superfamily (FGFs) (see Kawaguchi et al., (2007) J. Orthopaedic Res. 25(4): 480-487), members of the platelet derived growth factor superfamily (PDGFs) (see Hollinger et al., 2008 JBJS 90(s1):48-54), and vascular endothelial growth factor (VEGF) (Street et al., 2002 PNAS 99:9656-61).

For these growth factors to be effective they must be active and available at a sufficient concentration at the time when critical densities of the appropriate responsive cells are present in the repair site. The short half-life, thermal instability, sensitivity to proteases and/or solubility of the GFs requires their administration in combination with a carrier to achieve this requirement.

A number of carriers have been evaluated for the delivery of GFs. These include fibrous collagen sponges, gelatin hydrogels, fibrin gels, heparin, reverse phase polymers such as the poloxamers, carriers composed of poly-lactic acid (PLA), poly-glycolic acid (PGA) or their co-polymers (PLGA), heparin-conjugated PLGA carriers, and inorganic materials such as calcium phosphates. For example the bioimplant (GEM-21S®) which is used for periodontal regeneration uses beta tricalcium phosphate (β-TCP) as the carrier for rhPDGF-BB.

However, these carriers are of limited effectiveness, due to loss of growth factor activity when associated with the carrier, inefficient release of the GF at the implantation site, and/or poor protection from proteolysis and degradation. For example the bioimplant Infuse® uses a type I collagen sponge as the carrier for rhBMP-2. The rhBMP-2 is released in a burst from the carrier and the half life of the BMP within the wound site is 1-3 days (Winn et al., 1998, Adv. Drug Del. Rev. 31:303; Friess et. al., 1999, Intl. J. Pharm., 187:91). By the time the mesenchymal stem cells which regenerate bone have migrated into the wound site only fractions of a percent of the original amount of BMP loaded is present to stimulate these cells to make bone. The current solution to ensure an effective level of BMP remaining at these later times is to significantly increase the amount of BMP that is initially loaded. These increased doses increase the risk of complications including bone formation beyond the implant site, autoimmune responses and potentially cancer. Further this dramatically increases the cost of the implant.

Therefore, a need exists in the art for materials and methods which release growth factors with a profile which minimizes the amount of growth factor that needs to be loaded to achieve the required therapeutic effect.

One strategy is to encapsulate the GF in a biodegradable polymeric matrix that releases the GF with a sustained release profile over many days. For example BMPs have been combined with poly-lactic acid (PLA) or poly-lactic co-glycolic acid (PLGA) to produce sustained release profiles. However the incorporation of the BMP in the PLA or PLGA can denature the BMP reducing its activity and it is difficult to manipulate the release profile to optimize the effectiveness of the bioimplant. Further the degradation rate of these carriers is typically such that large amounts of GF remain locked away long after healing is complete. Consequently large amounts of GF need to be loaded into these polymers to ensure sufficient GF is present at the appropriate times.

Another strategy is to chemically immobilize the GF directly onto the surface of carrier. However this may result in partial or complete loss of activity of the GF, and may restrict the GF activity such that only those cells directly in contact with the carrier are able to interact with the GF and respond (see Steinmuller-Nethl, D. et al., Biomaterials, 2006, 27: 4547-56) which could be undesirable as the effect could be limited to the immediate interface with the carrier and not throughout the wound site.

The composition of the carrier can influence delivery of the GF. Calcium sulphate has been considered desirable as a bone substitute and GF carrier because it is osteoconductive, biodegradable, biocompatible and nontoxic (Chen et al., J. Craniofacial Surg., 2010, 21:188-197). However, calcium sulphate is also known to have a rapid degradation rate when added to bone in situ and little osteoinductive capability, which has limited its usefulness in bone implants.

One strategy to manage calcium sulphate degradation in situ has been to control degradation rate by altering crystal structures and adding polymers (e.g., chitosan) to the calcium sulphate implant mixture (Chen et al., supra). Polymer-coating calcium sulphate pellets that have been impregnated with BMP can decrease the speed of resorption of calcium sulphate and increase compressive strength and osteoinduction of the mixture (Chen et al., supra).

Composites containing hydroxyapatite (HAp), a major mineral component of bone, and calcium sulphate hemihydrate (CSH, plaster of Paris) have been used in orthopedic grafts (e.g., Damien, C et al., J. Biomed. Mat. Res., 1990, 24: 639-654; Damien, C et al., Spine, 2002, 16S: S50-S58; Parsons, J., et al., Annals N.Y. Acad. Sci.). When CSH is mixed with sterile saline or water it immediately begins to gel. While in the gel state HAp, growth factors and/or various matrix components can be mixed together with the CSH to form the graft composite, which can be inserted or injected into a bone defect where it sets in situ. In such methods, CSH initially acts as a binder. However, subsequent resorption of calcium sulphate leaves behind a porous matrix with space for bone in-growth, which can be stimulated by the growth factors in the hardened composite. Similarly, compositions for delivering osteogenic proteins including CSH, a porous particulate polymer mixture and an ostogenic protein are known (U.S. Pat. No. 5,385,887 and U.S. Patent Application Publication No. 2008/0233165, each of which is incorporated herein by reference as if set forth in its entirety). In each of these methods calcium sulphate degradation is required for growth factor release. Therefore, bone regeneration is dependent on the rate of calcium sulphate degradation.

Bone grafts containing particulate bone and a biocompatible solid component comprising CSH and a calcium phosphate product are known, but do not involve using the CSH or calcium phosphate as a growth factor carrier (U.S. Patent Application Publication No. 2011/0208305, incorporated herein by reference as if set forth in its entirety).

In nature during wound healing multiple GFs are present within the wound site and surrounding tissue at varying concentrations at different times. For example, immediately following bone fracture, platelets at the injury site will initially release large amounts of PDGF, with a sharp decline in protein levels within the fracture site over the following days (see Tyndall et al., Clinical Orthopedics and Related Research, 2003, 408: 319-330). Conversely BMP-2 is expressed at all stages of the fracture healing process (see Rasubala et al. British Journal of Oral and Maxillofacial Surgery, 2003, 41: 173-178), although the amount of BMP-2 varies over time (see Meyer et al. J Bone Jt. Surg 2003, 85-A: 1243-1254). The concentration of these growth factors is estimated to be orders of magnitude lower than those used during therapeutic application of exogenous GF due to matching of the concentration to the cellular requirements and synergistic effects of the multiple growth factors. Producing a system that allows the delivery of growth factors with multiphasic release profiles and the release of multiple growth factors with different release profiles would permit the use of bioimplants with GF release profiles that more closely mimic GF release during the natural healing process than current bioimplants that release a single growth factor in a burst or with sustained release.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention provides, in one aspect, a system, method and kit for the multiphasic release of at least one growth factor at, for example a treatment site. For this purpose, the system of the invention may be provided as a bioimplant or the like. In one aspect, the method of the invention delivers at least one growth factor in an initial release followed by the delivery of at least one growth factor in a "sustained release profile". The invention utilizes a delivery system for the initial release and a carrier for the sustained release.

In one aspect, the same growth factor is released in the initial and sustained release profiles. In another aspect, different growth factors are released, with a first growth factor released in an initial profile and a second growth factor released in a sustained release profile. As will be known to persons skilled in the art, the release of two different growth factors in such differing manners is believed to more closely mimic the natural growth factor release system at a treatment site.

In accordance with one aspect of the invention, there is provided a carrier that provides a sustained release of at least one growth factor, combined with a delivery vehicle that provides an initial release of at least one growth factor. The combination of the carrier and the delivery vehicle results in a multiphasic release profile of the growth factor(s). In preferred embodiments, the amount of carrier and delivery vehicle are varied to control the release of at least one GF, wherein the amount of the delivery vehicle and the carrier are provided in a ratio of about 0.5 to 4.0:1 (v:v). In preferred embodiments, the amount of delivery vehicle used is between 0.5 and 10.0 ml. In particularly preferred embodiments, 0.75-2.5 ml of delivery vehicle are used with 1 cm$^3$ of carrier. In particularly preferred embodiments, 1.0 ml of delivery vehicle and 0.5 cm$^3$ of carrier are used.

In preferred embodiments the growth factor ("GF") is a member of the transforming growth factor beta (TGFβ) superfamily. In particularly preferred embodiments the growth factor is a bone morphogenetic protein (BMP).

In one aspect of the present invention, the carrier ("CAR") is formed of calcium phosphate particles with a size less than 80 microns and preferably less than 45 microns dispersed within a polymer matrix which results in a larger structure. In one aspect, the structure is further coated with a hydroxyapatite layer.

In one embodiment the at least one GF is/are applied as a liquid to the calcium particles and are then lyophilized onto the particles before combining with the polymer matrix. In some embodiments, 100% of the lyophilized GF is associated with the particles. In other embodiments less than 100% of the lyophilized GF is associated with the particles and the remainder is not associated with the particles. Such composition comprising GF-associated particles and lyophilized GF that is not associated with particles can be combined with a delivery vehicle such that the unassociated particles are distributed in the delivery vehicle, where they can subsequently be released.

In another aspect of the present invention the carrier is formed by mixing one or more calcium phosphate powders with a liquid solution containing at least one growth factor to produce a calcium phosphate cement. In one aspect, the cement is then ground into particles with a diameter of at least 100 microns and preferably between 0.3 and 3 mm in diameter.

In another aspect of the present invention the carrier comprises particles of one or more calcium salts all with a diameter of at least 100 microns and preferably between 0.3 and 3 mm. A growth factor is then lyophilized onto the surface of the carrier particles.

In preferred embodiments the delivery vehicle is a reverse phase polymer. In particularly preferred embodiments the reverse phase polymer is a poloxamer, more particularly poloxamer 407 (also called Pluronic™ F127) at a concentration of at least 12% and preferably between 20 and 40%. In some particularly preferred embodiments, the amounts of P407 and carrier are varied to influence the amount of GF released from the carrier and optionally from the delivery vehicle.

As indicated above, in one aspect, the carrier and the delivery vehicle release the same growth factor while in another aspect, the carrier and delivery vehicle release different growth factors. In yet another aspect of the invention, the carrier and delivery vehicle are each adapted to release combinations of two or more growth factors, with the combination released by each being the same or different.

Thus, in one aspect, the invention provides a system for multiphasic release of growth factors at a treatment site, the system comprising:
 a delivery vehicle comprising at least one first growth factor; and
 a carrier comprising at least one second growth factor;

wherein:
 the delivery vehicle is adapted to release the at least one first growth factor in an initial release profile over a first time period;
 the carrier is adapted to release the at least one second growth factor in a sustained release profile over a second time period.

In another aspect, the invention provides a method of multiphasic release of growth factors, the method comprising:
 delivering at least one first growth factor with an initial release profile;
 delivering at least one second growth factor in a sustained release profile.

In a further aspect, the invention provides a kit for multiphasic delivery of growth factors, the kit comprising:
 a delivery vehicle component;
 at least one first growth factor associated with the delivery vehicle;
 a carrier component; and
 at least one second growth factor associated with the carrier.

In still a further aspect, the invention provides a kit for multiphasic delivery of growth factors, the kit comprising:
 a delivery vehicle component;
 a carrier component;
 at least one first growth factor that is not associated with the delivery vehicle or the carrier; and
 at least one second growth factor associated with the carrier.

In one embodiment, the kit comprises at least two containers, wherein the first container comprises the delivery vehicle and the second container comprises the carrier associated with the at least one second growth factor and the at least one first growth factor. In preferred embodiments, the at least one first growth factor mixes with the delivery vehicle when the delivery vehicle is added to the carrier.

The present invention also provides, in one aspect, a system, method and kit for the release of at least one growth factor, for example at a treatment site, wherein calcium sulphate "carrier" particles house the at least one growth factor on their surface. For this purpose, the system of the invention may be provided as a bioimplant or the like.

In one aspect, the method of the invention delivers the at least one growth factor in a "sustained release profile".

In one aspect of the present invention, the carrier comprises a mixture of calcium sulphate dihydrate and calcium phosphate particles. In preferred embodiments, the ratio of calcium sulphate to calcium phosphate particles is about 1:1 or 2:1.

In some aspects of the present invention, the at least one growth factor is released in a single phase from the calcium carrier. In this aspect, GF is not released by the delivery vehicle. In other aspects, the at least one growth factor undergoes multiphasic release from the calcium carrier and the delivery vehicle. In preferred embodiments, the amount of carrier and delivery vehicle are varied to control the release of at least one GF, wherein the amount of the delivery vehicle and the carrier are provided in a ratio of about 0.5-4:1 (v:v). In preferred embodiments, the amount of delivery vehicle used is between 0.5 and 10.0 ml. In particularly preferred embodiments, 0.5-2.5 ml of delivery vehicle is used per cm$^3$ of carrier. In particularly preferred embodiments, 1.0 ml of delivery vehicle and 0.5 cm$^3$ of carrier are used.

In one embodiment the at least one GF is/are applied as a liquid to the calcium particles and are then lyophilized onto the particles before combining with the polymer matrix.

In one embodiment the GF is lyophilized such that some of the GF is associated with the carrier and some of the GF is separate from the carrier. When the delivery vehicle is added to carrier the separate GF becomes associated with delivery vehicle.

In preferred embodiments, distribution of the at least one GF onto the calcium particles is altered by varying the volume of the solution containing the GF relative to the protein to be lyophilized onto the particles. The amount of bound GF on calcium particles can be made higher by decreasing the volume of solution used to deliver the GF. In preferred embodiments, lyophilization of GF onto carrier particles is carried out in a 1:1:0.5 ratio, wherein 1 unit of GF is mixed with 1 unit of solution and lyophilized onto 0.5 units of carrier. In particularly preferred embodiments, about 1.0 mg of GF is added to about 1.0 ml of solution for lyophilization onto about 0.5 cm$^3$ of calcium particles.

In a further aspect the invention provides a kit for delivery of growth factors, the kit comprising:
 a delivery vehicle component;
 a carrier component comprising a plurality of calcium sulphate particles;
 at least one second growth factor associated with the carrier and optionally,
 at least one first growth factor not associated with the carrier which will become associated with the delivery vehicle when the delivery vehicle is mixed with the at least one first growth factor In preferred embodiments, the carrier component of the kit further comprises calcium phosphate particles. In a particularly preferred embodiment, the ratio of calcium sulphate to calcium phosphate particles is about 1:1 or 2:1.

In a further aspect the invention provides a kit for multiphasic delivery of growth factors, the kit comprising:
 a delivery vehicle component;
 at least one first growth factor associated with the delivery vehicle;
 a carrier component comprising a plurality of calcium sulphate particles; and
 at least one second growth factor associated with the carrier.

In preferred embodiments, the carrier component of the kit further comprises calcium phosphate particles. In a particularly preferred embodiment, the ratio of calcium sulphate to calcium phosphate particles is about 1:1 or 2:1.

BRIEF DESCRIPTION OF THE DRAWINGS

The invention will now be described with reference to the appended figures, which are briefly described below.

DETAILED DESCRIPTION OF THE INVENTION

Figure 1:
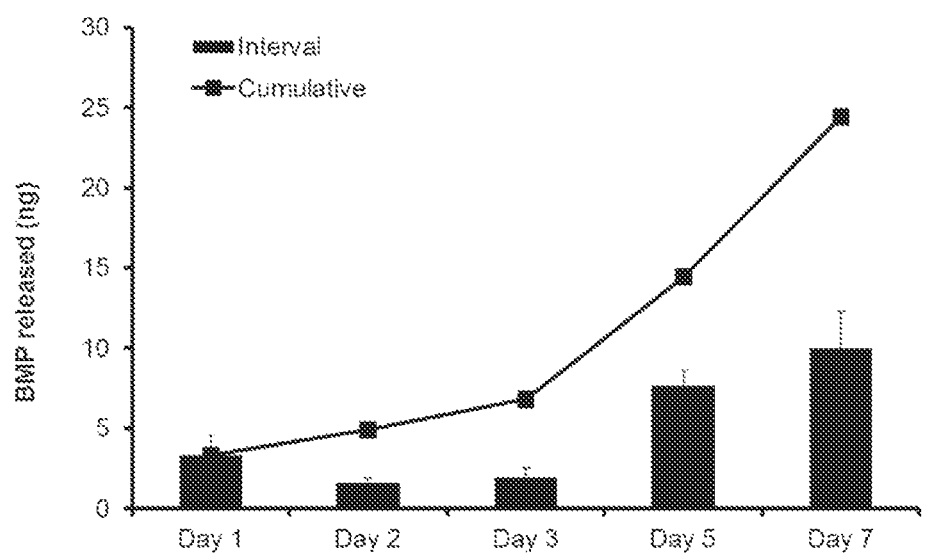
FIG. 1 illustrates a sustained release profile exhibited by the carrier of the invention.

Growth factors (GF) play an integral role in the repair and regeneration of tissues and exogenous GFs can be used to stimulate the repair of various tissues and organs. For exogenous growth factors to be effective in stimulating repair they must be retained at the site requiring repair, and be protected from inactivation, sequestration or degradation. To achieve this carriers are used. However the release of growth factors from known carriers is not ideal and cannot be easily modified. The current invention is based on: i) the discovery that the multiphasic release of growth factors from a bioimplant increases the efficacy of the implant; and ii) the discovery that the use of calcium sulphate as a growth factor carrier can improve the potency of GF containing bioimplants.

The present inventors have developed methods and materials for enhancing the efficacy of, for example, bioimplants by improving the release kinetics or release profile of growth factors at sites of implantation, while maintaining the activity of the growth factors. In one aspect, the present invention provides a growth factor delivery system and method comprising a carrier containing at least one growth factor, combined with a delivery vehicle also containing at least one growth factor. The at least one growth factor released by the carrier and delivery vehicle may be the same or different.

In another aspect, the present invention provides a growth factor delivery system and method that has enhanced efficacy due to using a carrier comprising a plurality of calcium sulphate dihydrate particles comprising at least one GF on their surface, combined with a delivery vehicle that may optionally contain at least one GF. In contrast, previous attempts to use calcium sulphate as a GF carrier involved incorporating or impregnating calcium sulphate particles with the growth factor rather than coating the surface of the calcium particles with a GF. In the present invention, calcium sulphate degradation is not required for GF release.

In preferred embodiments, the amount of carrier and delivery vehicle are varied to control the release of at least one GF, wherein the amount of the delivery vehicle and the carrier are provided in a ratio of about 0.5-4.0:1 (v:v). In preferred embodiments, the amount of delivery vehicle used is between 0.5 and 10.0 ml. In particularly preferred embodiments, 0.5-2.5 ml of delivery vehicle is used per cm³ of carrier. In particularly preferred embodiments, 1.0 ml of delivery vehicle and 0.5 cm³ of carrier are used.

In one embodiment the at least one GF is/are applied as a liquid to small (<80 micron) calcium particles and are then lyophilized onto the particles before combining with a polymer matrix to produce the carrier structure.

In another embodiment the GF is applied as a liquid to large (>100 micron) particles and then lyophilized with the particles resulting in a distribution of particle-associated and particle-free GF.

In preferred embodiments, distribution of the at least one GF between being associated with the particles and being separate or "free" from the particles is altered by varying the volume of the solution containing the GF relative to the amount of particles with which it is incubated prior to lyophilization. The amount of bound GF on particles can be made higher by decreasing the volume of solution used to deliver the GF. In preferred embodiments, lyophilization of GF onto carrier particles is carried out in a 1:1:0.5 ratio, wherein 1 unit of GF is mixed with 1 unit of solution and lyophilized onto 0.5 units of carrier. In particularly preferred embodiments, about 1.0 mg of GF is added to about 1.0 ml of solution for lyophilization onto about 0.5 cm³ of calcium particles.

The system and method of the invention can be used for a variety of therapeutic and clinical applications, including: fracture repair; bone grafts; spine fusion; and regeneration of skull, mandibular, and bone defects. For such applications, the system of the invention is preferably provided on, or in the form of a bioimplant.

DEFINITIONS

Unless defined otherwise below, all technical and scientific terms used herein have the same meaning as commonly understood by one of ordinary skill in the art to which this invention belongs.

As used herein the term "bioimplant" refers to a material which is suitable for implantation and contains an exogenous growth or biologically active factor. As discussed further herein, the system of the present invention is preferably used by applying same to a bioimplant. The bioimplant is then provided within a body of a subject wherein the system releases at least one growth factor in a multiphasic release profile.

As used herein the term "growth factor" refers to peptides and proteins that stimulate the growth and/or differentiation of cells via the interaction of the GFs with specific cell surface receptors. Examples of growth factors include the bone morphogenetic proteins (BMPs), transforming growth factor beta (TGFβ), the insulin-like growth factors (IGF), the fibroblast growth factors (FGFs), platelet derived growth factor (PDGF) and vascular endothelial growth factor. In preferred embodiments the growth factors are BMPs.

By "recombinant" is meant a protein produced by a transiently transfected, stably transfected, or transgenic host cell or animal as directed by an expression construct containing the cDNA for that protein. The term "recombinant" also encompasses pharmaceutically acceptable salts of such a polypeptide As used herein, the term "polypeptide" or "protein" refers to a polymer of amino acid monomers that are alpha amino acids joined together through amide bonds. Polypeptides are therefore at least two amino acid residues in length, and are usually longer. Generally, the term "peptide" refers to a polypeptide that is only a few amino acid residues in length. A polypeptide, in contrast with a peptide, may comprise any number of amino acid residues. Hence, the term polypeptide included peptides as well as longer sequences of amino acids.

As used herein, the terms "bone morphogenetic protein" or "bone morphogenic protein" or "BMP" are used interchangeably and refer to any member of the bone morphogenetic protein (BMP) subfamily of the transforming growth factor beta (TGFβ) superfamily of growth and differentiation factors, including BMP-2, BMP-3 (also known as osteogenin), BMP-3b (also known as growth and differentiation factor 10, GDF-10), BMP-4, BMP-5, BMP-6, BMP-7 (also known as osteogenic protein-1, OP-1), BMP-8 (also known as osteogenic protein-2, OP-2), BMP-9, BMP-10, BMP-11 (also known as growth and differentiation factor 8, GDF-8, or myostatin), BMP-12 (also known as growth and differentiation factor 7, GDF-7), BMP-13 (also known as growth and differentiation factor 6, GDF-6), BMP-14 (also known as growth and differentiation factor 5, GDF-5), and BMP-15.

The terms "bone morphogenetic protein" and "BMP" also encompass allelic variants of BMPs, function conservative variants of BMPs, and mutant BMPs that retain BMP activity. The BMP activity of such variants and mutants may be confirmed by any of the methods well known in the art (see the section Assays to measure BMP activity, below) or as described in Example 1

In preferred embodiments, the BMP is BMP-2, BMP-4, BMP-5, BMP-6, BMP-7, BMP-8 or BMP-9. In particularly preferred embodiments the BMP is BMP-2, BMP-4 or BMP-7.

In preferred embodiments the BMP is a mammalian BMP (e.g., mammalian BMP-2 or mammalian BMP-7). In particularly preferred embodiments, the BMP is a human BMP (hBMP) (e.g. hBMP-2 or hBMP-7).

As used herein the term "scaffold" refers to a material whose purpose is to provide a structure which supports cell adhesion, migration and ingrowth into a tissue repair site.

As used herein the term "carrier" refers to a material comprising single or multiple components and is adapted to release at least one growth factor at a treatment site in a "sustained release" profile over a period of time. In one aspect, the period of time taken by the carrier to release the at least one growth factor is between several days and several weeks. Preferably, the carrier is adapted to release the at least one growth factor over a period of weeks.

In preferred embodiments the carrier also acts as a scaffold or matrix. As discussed above, in one aspect of the invention, the carrier is formed of calcium phosphate particles dispersed within a macroporous polymer scaffold or matrix. In one aspect, the scaffold or matrix is further coated with a hydroxyapatite layer. In another aspect of the invention, the carrier is formed of calcium sulphate particles. In yet another aspect of the invention, the carrier is a mixture of calcium sulphate and calcium phosphate particles. In one embodiment the at least one growth factor is applied as a liquid to the calcium particles and then lyophilized onto the particles before combining the particles with the polymer matrix. In preferred embodiments, the carrier is a solid.

As used herein the term "delivery vehicle" refers to a material which serves to transport the carrier. In one aspect of the invention, the delivery vehicle comprises or becomes associated with at least one growth factor and is adapted to release the at least one growth factor at a treatment site in an initial release profile over a time period. In other aspects, the delivery vehicle does not initially comprise a growth factor.

Rather, it is subsequently combined with a GF that is not associated with the carrier prior to use, thereby producing the initial phase of GF release. In one aspect, the period of time taken by the delivery vehicle to release the at least one growth factor is between several hours and several days. In a preferred embodiment of the invention, the delivery vehicle releases the majority of the at least one growth factor in an "initial release" or "initial release profile" that lasts a period of hours. Preferably, the delivery vehicle is adapted to release at least 80% of the growth factor(s) contained therein (or associated therewith) within a period of 72 hours. In preferred embodiments, the delivery vehicle is a liquid or a gel.

In one aspect, the delivery vehicle of the present invention may be used to ease handling of the carrier particles, wherein the combination of the carrier and delivery vehicle results in the formation of a gel or putty.

In one aspect, the material forming the delivery vehicle is in the form of a gel. In preferred embodiments the delivery vehicle is a reverse phase polymer. As used herein the term "reverse phase" refers to the property whereby the polymer undergoes a reversible temperature dependent transition from a liquid to a gel. In one aspect the transition temperature is between 15° C. and 37° C. Preferably the transition temperature is between 15° C. and 25° C. As would be known to persons skilled in the art, "normal phase" materials increase their viscosity with a decline in temperature. In contrast, reverse phase materials show a decline in viscosity as the temperature drops below their transition temperature.

In particularly preferred embodiments the reverse phase polymer is a poloxamer, more particularly Pluronic™ F127 (also known as poloxamer 407 or P407).

In particularly preferred embodiments the P407 polymer solution is between 20 and 40%

In preferred embodiments, the amount of carrier and delivery vehicles used in a bioimplant are altered to influence the amount of GF released from the bioimplant.

As used herein the term "sustained release" or "sustained release profile" refers to the release of at least one growth factor, by the carrier, over a period of several days or weeks with the amount released over an initial period being similar to or less than the amount released over the same period after several days or weeks of implantation. Preferably, a sustained release profile lasts at least one week. As will be understood by persons skilled in the art, typically, the amount of growth factor released in a sustained release profile over the first three days will be less than the amount released over the following seven days.

Figure 2:
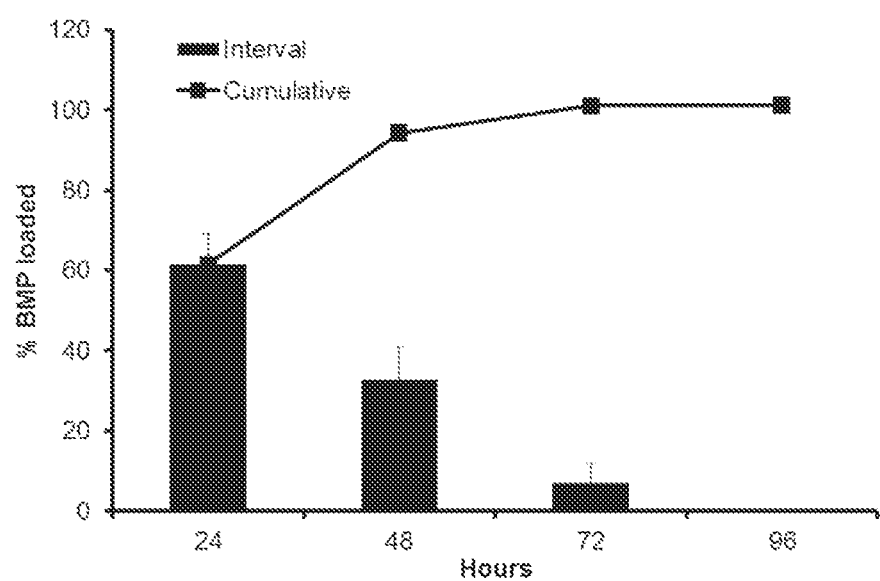
FIG. 2 illustrates the initial release profile exhibited by the delivery vehicle of the invention.

As used herein the term "initial release" or "initial release profile" refers to the initial release, by the delivery vehicle, of a large amount of at least one growth factor followed by progressively smaller amounts released over a period of hours or days. In one aspect, an initial release profile results in the delivery of at least 80% of the loaded growth factor(s) within a period of roughly 72 hours. An initial release profile is illustrated in FIG. 2.

As used herein the term "multiphasic release" refers to an initial release of the at least one growth factor over an initial period of time, followed by "sustained" release of the at least one growth factor over a second period of time. Preferably, the initial period of time is roughly several hours and the second period of time is roughly several days to weeks. Such a release profile may also be referred to as "biphasic release" since it occurs in two stages. In preferred embodiments, the initial release is provided by the delivery system of the invention and the "sustained" release is provided by the carrier of the invention.

As used herein, the term "potency" refers to a measure of drug activity expressed in terms of the amount required to produce an effect of given intensity In one aspect of the invention, the delivery vehicle component comprises at least 10% and not more than 50% of the total amount of growth factor(s) delivered by the system of the invention and the carrier component comprises at least 50% of the total amount of growth factor(s) delivered by the system.

Assays to Measure BMP Activity

Assays to characterize in vitro and in vivo function of recombinant BMPs are well known in the art, (see, e.g., U.S. Pat. No. 4,761,471; U.S. Pat. No. 4,789,732; U.S. Pat. No. 4,795,804; U.S. Pat. No. 4,877,864; U.S. Pat. No. 5,013,649; U.S. Pat. No. 5,166,058; U.S. Pat. No. 5,618,924; U.S. Pat. No. 5,631,142; U.S. Pat. No. 6,150,328; U.S. Pat. No. 6,593,109; Clokie and Urist, Plast. Reconstr. Surg. 2000; 105:628-637; Kirsch et al., EMBO J 2000; 19:3314-3324; Vallejo et al., J. Biotech. 2002; 94:185-194; Peel et al., J. Craniofacial. Surg. 2003; 14:284-291; and Hu et al., Growth Factors, 2004; 22:29-33).

Such assays include: in vivo assays to quantify osteoinductive activity of a BMP following implantation (e.g., into hindquarter muscle or thoracic area) into a rodent (e.g. a rat or a mouse) (see, for example, U.S. Pat. No. 4,761,471; U.S. Pat. No. 4,789,732; U.S. Pat. No. 4,795,804; U.S. Pat. No. 4,877,864; U.S. Pat. No. 5,013,649; U.S. Pat. No. 5,166,058; U.S. Pat. No. 5,618,924; U.S. Pat. No. 5,631,142; U.S. Pat. No. 6,150,328; U.S. Pat. No. 6,503,109; Kawai and Urist., Clin. Orthop. Relat. Res., 1988; 222:262-267; Clokie and Urist, Plast. Reconstr. Surg., 2000; 105:628-637; and Hu et al., Growth Factors, 2004; 22:29-33); in vivo assays to quantify activity of a BMP to regenerate skull trephine defects in mammals (e.g., rats, dogs, or monkeys) (see, for example, U.S. Pat. No. 4,761,471 and U.S. Pat. No. 4,789,732); in vitro assays to quantify activity of a BMP to induce proliferation of in vitro cultured cartilage cells (see, for example, U.S. Pat. No. 4,795,804); in vitro assays to quantify activity of a BMP to induce alkaline phosphatase activity in in vitro cultured muscle cells (e.g., C2C12 cells, ATCC Number CRL-1772) or bone marrow stromal cells (e.g., murine W-20 cells, ATCC Number CRL-2623) (see, for example, U.S. Pat. No. 6,593,109; Ruppert et al., Eur J Biochem 1996; 237:295-302; Kirsch et al., EMBO J, 2000; 19:3314-3324; Vallejo et al., J Biotech, 2002; 94:185-194; Peel et al., J Craniofacial Surg., 2003; 14:284-291; and Hu et al., Growth Factors, 2004; 22:29-33); in vitro assays to quantify activity of a BMP to induce FGF-receptor 2 (FGFR3) expression in cultured mesenchymal progenitor cell lines (e.g., murine C3H10T1-2 cells) (see, for example, Vallejo et al. J Biotech 2002; 94:185-194); in vitro assays to quantify activity of a BMP to induce proteoglycan synthesis in chicken limb bud cells (see, for example, Ruppert et al., Eur J Biochem 1996; 237:295-302); and in vitro assays to quantify activity of a BMP to induce osteocalcin treatment in bone marrow stromal cells (e.g., murine W-20 cells; ATCC Number CRL-2623) (see, for example, U.S. Pat. No. 6,593,109).

Assays to Measure BMP Binding and Release

Various assays can be used to measure binding and release of recombinant BMP from a carrier. For example, the amount of recombinant BMP protein can be quantified by any of the techniques well known in the art, including dot blots, immunoassay (e.g., enzyme linked immunosorbent assays, ELISA), measurement of the increase in radioactivity present in the release buffer when the bioimplant incorporates radiolabeled BMP and chromatography (e.g., high pressure liquid chromatography, HPLC and ion-exchange chromatography).

Such methods are well known in the art (See for example, Harlow and Lane, Using Antibodies: A Laboratory Manual, Cold Spring Harbor Laboratory Press. 1999; Gosling, ed., Immunoassays: A Practical Approach, Oxford University Press. 2000; Oliver, ed., HPLC of Macromolecules: A Practical Approach., Oxford University Press, 1998; Millner, ed., High Resolution Chromatography: A Practical Approach. Oxford University Press, 1999; Hockfield et al., Selected Methods for Antibody and Nucleic Acid Probes. Cold Spring Harbor Laboratory Press. 1993; Gore, ed., Spectrophotometry and Spectrofluorimetry: A Practical Approach. Oxford University Press, 2000).

For example, protocols for radioimmunoassay analysis of BMP proteins have been described (see, for example, U.S. Pat. No. 4,857,456). For example, protocols for immunoblot analysis of BMP proteins have been described (see, for example, Wang et al. Proc Natl Acad Sci USA 1990; 87:2220-2224). For example, ELISA kits for the quantitation of protein levels of human, rat, or mouse BMP-2 are commercially available, for example, from R&D Systems (catalog #DBP200, PDBP200, or SBP200). For example, ELISA kits for the quantitation of protein levels of human BMP-7 are commercially available, for example, from R&D Systems (catalog #DY354 or DY354E).

Kits

In one aspect, the invention provides a kit for containing the system described herein. In one embodiment, the kit comprises the necessary components for making the delivery vehicle and the carrier as well as the needed growth factors. That is, the kit of the invention would comprise the necessary components for making the delivery vehicle and the carrier as well as least one growth factor that is associated with, or subsequently will become associated with, the delivery vehicle and at least one growth factor associated with the carrier.

The kit preferably comprises a container comprising the carrier onto which may be loaded or coated the associated growth factor(s).

Preferably, the delivery vehicle and any associated growth factor(s) are maintained in separate containers, that can be combined at the time of use. This would be particularly preferable in cases where the delivery vehicle may comprise a liquid or a gel. In such case, where the delivery vehicle comprises both associated growth factor(s) and a liquid or gel, the associated growth factor(s) may be kept in a separate container as a lyophilized powder. At the time of use, the growth factor(s), in powder form, may be combined with the liquid or gel delivery vehicle.

In a preferred embodiment, the kit of the invention would comprise at least three containers for each of the following: 1) the delivery vehicle component; 2) the at least one first growth factor (i.e. the growth factor(s) associated with the delivery vehicle); and, 3) the carrier and the least one second growth factor (i.e. the growth factor(s) associated with the carrier). In use, the at least one first growth factor, in powder form, is combined with the liquid or gel form delivery vehicle and the mixture is then applied to the carrier onto which the at least one second growth factor was pre-loaded.

In another preferred embodiment, the kit of the invention would comprise at least two containers each comprising of the following: 1) the delivery vehicle component; and 2) the calcium sulphate carrier and the least one growth factor associated with the carrier and other growth factor that is not associated with the carrier. In use, the liquid or gel form delivery vehicle is applied to the carrier and associated GF (bound or loaded GF) and to the growth factor that is not associated with the carrier ("free" GF). The free GF then becomes incorporated into the delivery vehicle.

In one preferred embodiment, the carrier is comprised of a mixture of calcium sulphate and calcium phosphate particles. In particularly preferred embodiments of the present invention, the carrier is comprised of a mixture of calcium sulphate and calcium phosphate particles in a ratio of about 1:1 or 2:1. Preferably the carrier is coated with the at least one growth factor.

In yet another preferred embodiment, the kit of the invention would comprise at least three containers for each of the following: 1) the delivery vehicle component; 2) the at least one first growth factor (i.e. the growth factor(s) associated with the delivery vehicle); and, 3) the calcium sulphate carrier and the least one second growth factor (i.e. the growth factor(s) associated with the carrier). In use, the at least one first growth factor, in powder form, is combined with the liquid or gel form delivery vehicle and the mixture is then applied to the carrier onto which the at least one second growth factor was pre-loaded.

In one preferred embodiment, the carrier is comprised of a mixture of calcium sulphate and calcium phosphate particles. In particularly preferred embodiments of the present invention, the carrier is comprised of a mixture of calcium sulphate and calcium phosphate particles in a ratio of about 1:1 or 2:1. Preferably the carrier is coated with the at least one growth factor.

In one aspect, the kit of the invention may comprise any necessary reagents and/or instruments and/or instructions and/or vessels as may be needed.

EXAMPLES

The present invention will now be described by means of the following examples. These examples illustrate the novel findings by the inventors that a multiphasic release profile of a growth factor, such as rhBMP-2 produced by loading part of the BMP within a carrier that releases BMP with a sustained release and part of the BMP within a delivery vehicle that releases BMP with an initial release is more effective than carriers that only produce a burst release or a sustained release. These examples also illustrate that calcium sulphate dihydrate or a mixture of calcium sulphate dihydrate and calcium phosphate can be used as a carrier of a growth factor, such as BMP, in improved systems, methods and compositions for increasing the potency of the bioimplant.

As will be obvious to one skilled in the art it is possible to place one growth factor within the carrier and a different growth factor within the delivery vehicle, resulting in different release profiles of each growth factor.

It will be understood that the examples provided herein are intended solely to illustrate the present invention and not to limit the scope of the invention in any way. Likewise, the invention is not limited to any particular preferred embodiments described herein. Indeed, many modifications and variations of the invention may be apparent to those skilled in the art upon reading the present specification. The invention is therefore to be limited only by the terms of the appended claims, along with the full scope of equivalents to which the claims are entitled.

Example 1: Manufacture of a Sustained Release Composite Carrier Containing BMP by Encapsulation in PLGA This example demonstrates how to form a carrier containing rhBMP-2 and which releases the growth factor in a sustained release profile.

Materials and Methods

PLGA 75/25 with inherent viscosity of 1.33 dL/g (MW=205,000-210,000) was purchased from Birmingham Polymers Inc. (Birmingham, Ala.). Tetracalcium phosphate (TTCP) was obtained from Taihei Chemical Industrial Co. (Osaka, Japan) and dicalcium phosphate anhydrous (DCPA) and dimethyl sulfoxide (DMSO) were obtained from Sigma Chemical Co. (MO, USA). Sugar particles were purchased from Tate & Lyle North America Inc. (Toronto, Canada).

Resorbable calcium phosphate particles were prepared by mixing equimolar TTCP and DCPA with deionized distilled water (ddH2O) at 100% relative humidity for 24 h. The reactant was ground and sieved through 45 μm sieve.

Recombinant human BMP-2 (rhBMP-2, Induce Biologics Inc) in was prepared in formulation buffer (1.5 mg/ml, pH 4.5; 5 mm glutamic acid, 2.5% glycine, 0.5% sucrose and 0.01% Tween™ 80 with ddH$_2$O). The protein solution was added to vials containing CaP powder and agitated for at least 15 minutes. The powder was then frozen and lyophilized.

Particles with (CaP-BMP) or without (CaP) BMP were then used to make CaP particulate-PLGA scaffold blocks by phase-inversion/particle leaching as follows: PLGA was dissolved in DMSO at a concentration of 11.5% (w/v). To this solution, the CaP and CaP-BMP particles were thoroughly mixed according to a CaP/PLGA ratio of 2:1 (w/w). Sugar crystals with size ranges of 0.85-1.18 mm were dispersed in the CaP/PLGA and the mixture was solidified at −18° C. in a mold. The PLGA was precipitated and the sugar crystals leached out by soaking in three changes of ddH$_2$O.

A layer of hydroxyapatite was deposited onto and throughout the macroporous composite scaffolds as follows: dry PLGA/CaP cylinders, measuring 2 mm in diameter and 2 mm in length, were pre-wetted in 70% ethanol and immersed in 60 ml of 3×SBF for a period of 9 days at 37° C. SBF was prepared as follows: to 1.8 L of ddH2O under vigorous stirring the following salts were added sequentially 29.711 g NaCl, 2.206 g CaCl$_2$-2H$_2$O, 10 ml 1M HCl, 0.852 Na$_2$HPO$_4$. The final volume was brought to 2 L. The SBF solution was changed daily. Following coating, the 3PCC samples were rinsed in ddH$_2$O and air dried.

This resulted in the formation of a macroporous composite carrier (3PS) that is able to release rhBMP-2 with a sustained release profile over at least seven days. These results are illustrated in FIG. 1.

Example 2: Manufacture of a Sustained Release Carrier Containing BMP by Encapsulation in a Calcium Phosphate Cement The present example demonstrates how to form a calcium phosphate cement (CPC) carrier containing rhBMP-2 that has a sustained release profile.

Materials and Methods

Tetracalcium phosphate (TTCP) was obtained from Taihei Chemical Industrial Co. (Osaka, Japan) and dicalcium phosphate anhydrous (DCPA) was obtained from Sigma Chemical Co. Macroporous biphasic calcium phosphate granules (Eclipse) were purchased from Citagenix (Laval Qc, Canada). Recombinant human BMP-2 (rhBMP-2, Induce Biologics Inc) was prepared in formulation buffer (1.5 mg/ml, pH 4.5; 5 mm glutamic acid, 2.5% glycine, 0.5% sucrose and 0.01% Tween™ 80 with ddH2O).

Resorbable calcium phosphate cement particles were prepared by mixing equimolar TTCP and DCPA with rhBMP-2 solution. The reactant was ground and sieved through a 300 and 100 μm sieve and particles between 100 and 300 μm, retained.

This resulted in the formation of calcium phosphate cement carrier particles into which the rhBMP-2 was incorporated. Upon implantation into an animal BMP is released in a sustained manner over a period of at least several weeks.

To produce a CPC based sustained release carrier that also acted as a macroporous carrier CPC particles (0.1 to 0.3 mm) were mixed macroporous calcium phosphate granules (1-2 mm) in a 1:1 ratio (w/w).

Example 3: Manufacture of a Sustained Release Carrier Containing BMP by Use of a Coating that Binds BMP The present example demonstrates how to form a carrier that has a sustained release profile by applying a BMP binding coating. One such method is to coat a carrier with an antibody or BMP binding protein as described in our co-pending application number U.S. application Ser. No. 13/002,444 (the entire content of which is incorporated herein by reference).

Materials and Methods

Purified polyclonal rabbit anti-human BMP-2 antibodies were purchased from Cell Sciences, (Canton Mass., Cat #PA0025). Macroporous biphasic calcium phosphate (BCP) granules (Eclipse) were purchased from Citagenix (Laval, Qc, Canada.)

Sterile BCP granules were weighed out in a biosafety cabinet and placed in sterile TPP tubes (Mandel Scientific, Guelph ON, Canada). The antibody solution was diluted in phosphate buffered saline to final concentration of 150, 300 and 600 ng of antibody in 1 ml PBS, filter sterilized and applied to the carrier at a 1:1 v/v ratio. The samples were agitated for at least 15 minutes at room temperature, before being frozen and lyophilized. BMP solution was then applied to the granules, allowed to soak for 15 minutes at room temperature and then frozen and re-lyophilized.

This resulted in the formation of a BCP granules coated with antibody that bound and slowly released the rhBMP-2 in a sustained fashion.

The amount of rhBMP-2 that can be bound can be increased by increasing the amount of antibody used. The rate of release can be increased by using antibodies with lower affinity or avidity.

Example 4: Production of a BMP Containing Delivery Vehicle Using F127

The present example demonstrates how to prepare a delivery vehicle containing rhBMP-2 using F127.

Materials and Methods

Poloxamer was prepared as follows: 100 ml of distilled water was chilled to 4° C. and various amounts of poloxamer 407 were added slowly with stirring over a period of several hours, until all the solid prill was dissolved making a final solution ranging between 12 and 33%. The poloxamer solution was then sterilized in an autoclave (121° C., 20 minutes, 30 psi). Following sterilization, the poloxamer solution was kept at 4° C. until use.

Lyophilized recombinant human BMP-2 powder (rh-BMP-2, Induce Biologics Inc) was added to the poloxamer solution and was slowly mixed.

Alternatively rhBMP-2 was added from solution (1 mg/ml, pH 4.5; 5 mm glutamic acid, 2.5% glycine, 0.5% sucrose and 0.01% Tween 80) at a 1/10 or 1/20 ratio (v/v).

This resulted in the formation of a delivery vehicle that released more than 80% of the rhBMP-2 over the first two days (as illustrated in FIG. 2).

Example 5: Production of a Bioimplant with a Multiphasic Release Profile

The present example demonstrates how to form a 3PS-F127 bioimplant containing rhBMP-2 that releases the rhBMP-2 with a multiphasic release profile.

Materials and Methods

The 3PS carrier (as described in Example 1) containing 0, 4.55 or 9.1 µg of rhBMP-2 per 5 mg of carrier was prepared and stored in Eppendorf tubes. A delivery vehicle containing 0, 4.55 or 9.1 µg of rhBMP-2 in 45.5 µl F127 (prepared as described in Example 4) was stored in Eppendorf tubes at 4° C. Immediately prior to use, the F127 was pipetted onto the 3PS carrier and the carrier was mixed into the delivery vehicle.

This 3PS-F127 bioimplant was then used to measure BMP release in vitro and bone formation activity in vivo as described below.

The ratios of carrier to delivery vehicle can be varied to produce gel (1:1 ratio v:v) or putties (2:1 ratio v:v). Further the ratio of BMP to carrier or the particle size of the carrier can be varied to alter the sustained release profile. Finally the amount of rhBMP-2 in the carrier and the delivery vehicle can be varied to alter the amount of rhBMP-2 released initially over the first few hours compared to amount released over the following weeks.

Example 6: An In Vitro Assay for Release of BMPs from Bioimplants

The present example describes how to measure the release of rhBMP-2 from the various bioimplants described in Examples 1 to 5.

Materials & Methods

Bioimplants containing known amounts of rhBMP-2 prepared as in Examples 1 to 5 were transferred to Eppendorf tubes. The total amount of rhBMP-2 used was 9.1 µg of rhBMP-2 per 5 mg of carrier and 45.5 µl of F127, or 20 µg of rhBMP-2 to 10 mg of carrier to 100 µl of F127.

Samples were then incubated under agitation with a 1 ml solution of release buffer comprising phosphate buffered saline (PBS)+1% BSA at 37° C. The buffer was removed and replaced with fresh release buffer after various times (e.g. 1, 2, 5, 7 and 10 days) and the collected solutions were stored with 1.5 ml vials at −20° C. for further analysis.

The amount of BMP-2 released into the buffer was measured using a commercial ELISA (Quantikine™ hBMP-2 ELISA, RnD Systems). The ELISA was carried out according to the manufacturer's instructions.

Results

No BMP was detectable in release buffer collected from any of the bioimplants which had not been loaded with BMP. The carrier samples which had been loaded with rhBMP-2 demonstrated a sustained release of rhBMP-2 over the period of the study, while samples in the delivery vehicle alone were released in an "initial release profile".

When the carrier and delivery vehicle were combined, various release profiles were obtained depending on which component the BMP was loaded into. When 100% of the rhBMP-2 (9.1 µg) was loaded within the 3PS (5 mg) carrier which was then mixed with 33% F127 (45.5 µl), the BMP release profile matched the sustained pattern, where the amount of BMP released over the first 2 days was 5 ng, between days 3 and 5 it was 8 ng and between days 5 and 7 it was 10 ng (FIG. 3; 100-0).

Figure 3:
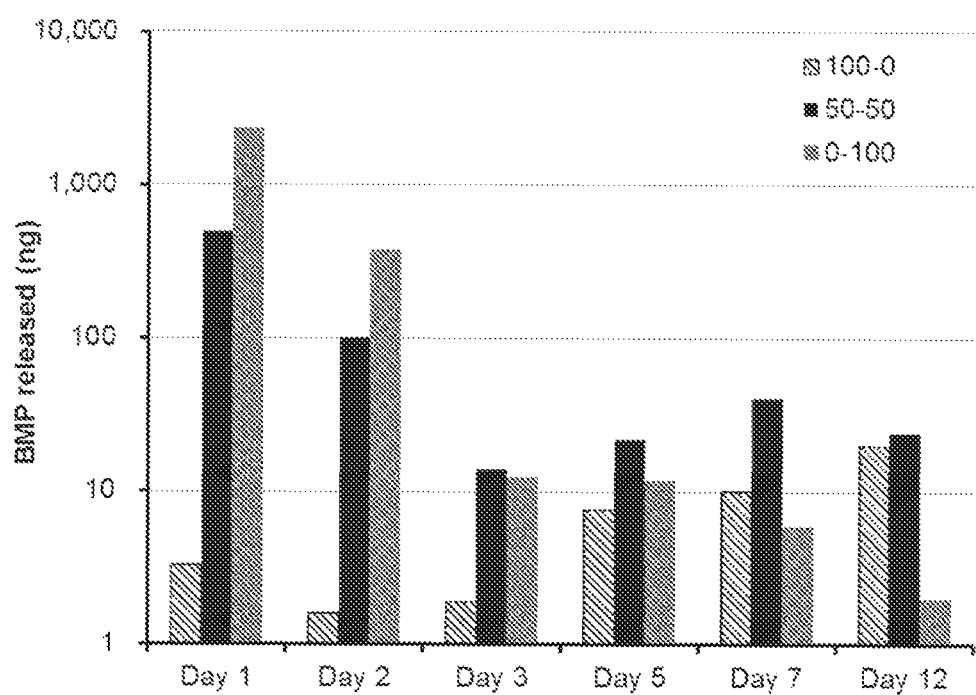
FIG. 3 illustrates differing release profiles based on an amount of growth factor in the delivery vehicle and carrier. A multiphasic release profile is observed when growth factors are incorporated into both the delivery vehicle and carrier (50-50).

When 100% of the rhBMP-2 (9.1 µg) was loaded within 33% F127 (45.5 µl) and then was then mixed with the 3PS carrier (5 mg) which had no BMP within it, the BMP was released where the amount of BMP released over the first 1 day was 2363 ng, over the second day was 381 ng and then 12 ng on the third day (FIG. 3; 0-100).

When the BMP was distributed between the carrier and the delivery vehicle the bioimplant demonstrated a biphasic release profile, with an intermediate initial release followed by sustained release of BMP (FIG. 3; 50-50).

Example 7: An In Vitro Assay to Test the Activity of Released BMPs

The present example describes how to determine whether the rhBMP-2 released from the bioimplants retains its activity. To demonstrate that the released rhBMP is biologically active, responsive cells can be cultured in with the releasate and their response to the growth factor measured. Such assays are known in the art (see Peel et al., J. Craniofac. Surg. 2003, 14:284-291).

Materials & Methods

Materials with or without rhBMP-2 as described in Examples 1 to 5 were prepared. Releasates were prepared as described in Example 3 except the buffer was alpha minimal essential medium with 15% fetal bovine serum and antibiotics (aMEM+15% FBS+AB)

C2C12 cells were seeded into 24 well tissue culture plates at $0.5 \times 10^5$ cells/ml, 1 ml alpha MEM+15% FBS per well. After various periods between 24 and 72 hours the media was removed and the various releasates were applied. Negative controls included C2C12 cells cultured with fresh aMEM+15% FBS+AB. Positive controls included C2C12 cells incubated with aMEM+15% FBS+AB containing 25, 50 and 100 ng/ml rhBMP-2. After 48 hours the cells were lysed in 1 ml cell lysis buffer (Cellytic Sigma Aldrich) and the alkaline phosphatase (ALP) activity of the cell lysates measured using the para-nitrophenol phosphate assay (Sigma Aldrich). The cell protein content of the lysates was measured using Coomassie Plus Reagent (Fisher) and was used to normalize ALP activity to the number of cells in each well.

Generally, to determine whether there has been any loss in activity of the BMP when associated with the carrier or delivery vehicle, a standard activity curve of ALP/PTN results for rhBMP-2 standards which have not been associated with the carrier or delivery vehicle is determined. The concentration of active rhBMP-2 in the releasates can be determined from this standard curve and this is expressed as a percentage of the total the amount of rhBMP-2 present in the releasates as determined by ELISA.

Example 8: Evaluation of Osteoinductive Activity of Multiphasic BMP Implants The present example describes how to determine the osteoinductive activity of BMP containing bioimplants in vivo. To evaluate the ability of bioimplants to induce bone formation the mouse muscle pouch assay was used. In this model the bioimplant is placed in a muscle pouch made in the hind limbs of the mouse and the size of the induced bone formed is proportional to the amount of BMP tested. Such assays are known in the art (see for example Barr et al., Oral Surg. Oral Med. Oral Pathol. Oral Radiol. Endod., 2010; 109:531-40.)

Materials and Methods

Bioimplants were prepared as described in Examples 1 and 5. Under anesthesia bilateral pouches were made in the thigh muscles of the hind limbs of male CD-1 mice aged 37-42 days, by blunt dissection. The bioimplants were then placed into sterile gelatin capsules which had been placed into the muscle pouch. The muscle was pulled together and the skin closed with Mitchel clips.

The animals were euthanized on post-op day 28. The hind limbs were harvested and fixed with 10% buffered formalin. Following fixation, the specimens were imaged using a microCT scanner (General Electric Healthcare eXplore™ Locus SP). Samples were scanned and reconstructed using the manufactures software at a resolution of 59 µm. Following image reconstruction, a region of interest (ROI) was determined. This area encompassed all areas containing the bioimplant induced bone. These can be easily distinguished from the skeletal bones based on location and density.

In order to analyze the quantity and quality of bone within the ROI, the voxels of the mCT images were segmented into bone and non-bone phases. Segmentation was achieved by determining a threshold value for the voxel grayscale at which the voxel was counted as bone. The total volume (TV), bone volume (BV), mineral density of the total volume (TV-MD), mineral density of the bone volume (BV-MD), mineral content of the total volume (TV-MC), mineral content of the bone volume (BV-MC) and bone volume fraction (BVF) of the ROI were determined for each sample. Values were adjusted for the presence of calcium due to the carrier by using an upper threshold value that selected only carrier and subtracting it from the values obtained using a lower threshold which included carrier plus new bone (see Humber et al., Oral Surgery, Oral Medicine, Oral Pathology, Oral Radiology, and Endodontology. 2010. 109:372-384).

Following completion of the microCT analysis, the specimens were either embedded in spurs resin or decalcified in formic acid and embedded in wax. Resin embedded samples were evaluated by backscatter SEM while wax embedded samples were cut and stained with hematoxylin and eosin (H&E) and examined by light microscopy to evaluate the tissue types present at the implantation site.

Results

A carrier and a delivery vehicle were combined as described in Example 5.

Figure 4:
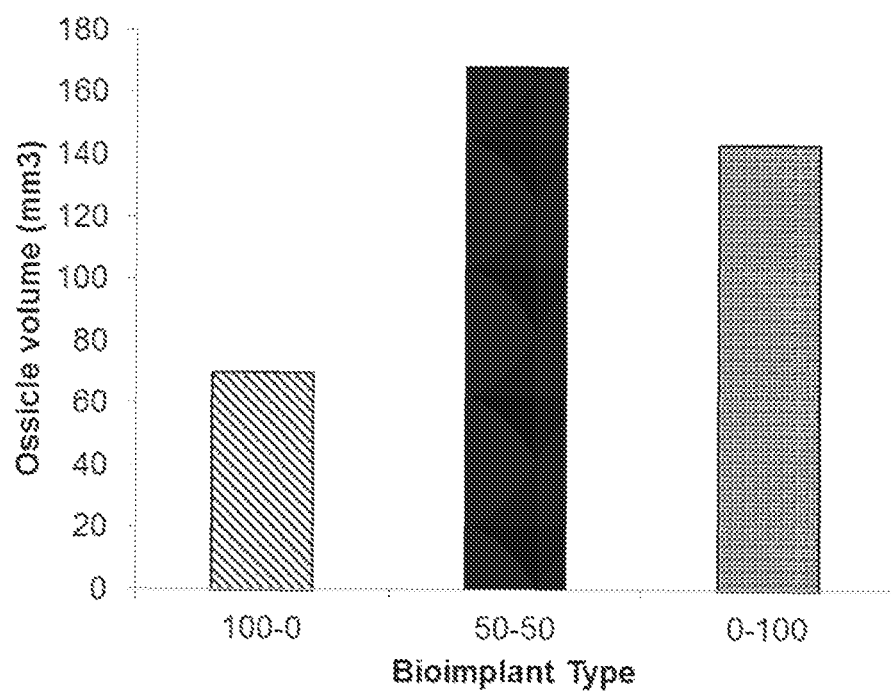
FIG. 4 illustrates the in vivo activity of the bioimplants where a growth factor is released as shown in FIG. 3 according to the method of the invention.

MicroCT analysis showed that bioimplants with all of the BMP within the 3PS carrier, which had a sustained BMP release profile, produced the smallest ossicles of bone (FIG. 4; 100-0), bioimplants with all of the BMP within the F127 delivery vehicle, which had a burst BMP release profile produced intermediate sized ossicles (FIG. 4; 0-100), while bioimplants with 50% of the BMP loaded into the carrier and 50% loaded into the delivery vehicle, which had a multiphasic BMP release profile, produced the largest ossicles of bone (FIG. 4; 50-50).

Figure 5:
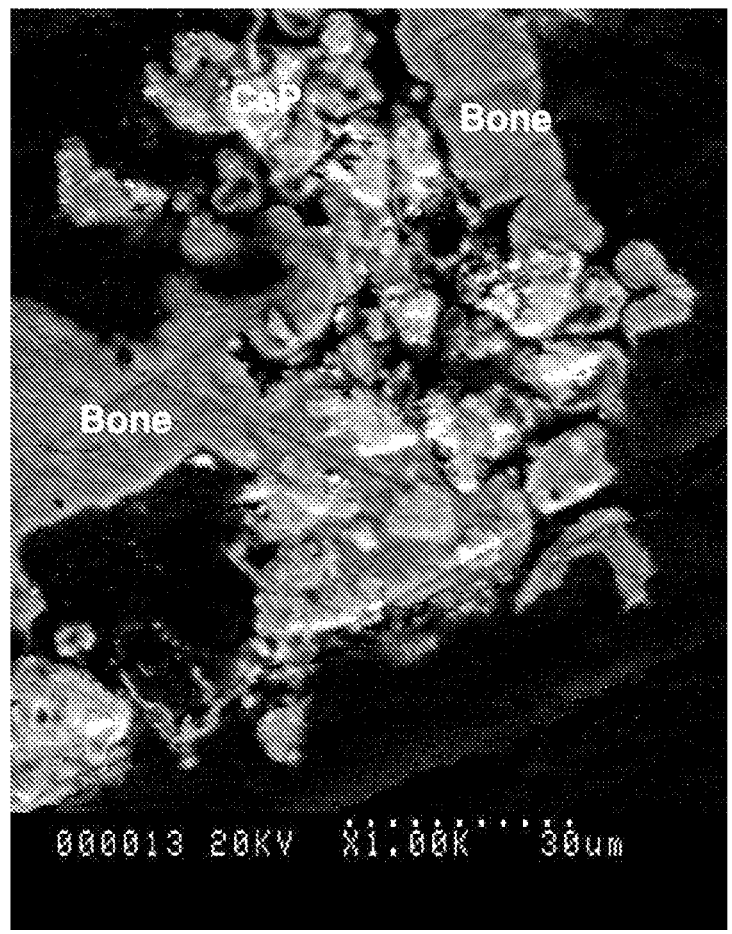
FIG. 5 illustrates the formation of new bone (Bone) onto calcium phosphate particles (CaP) when a bioimplant produced according to the method of the invention was implanted into a mouse.
Figure 6:
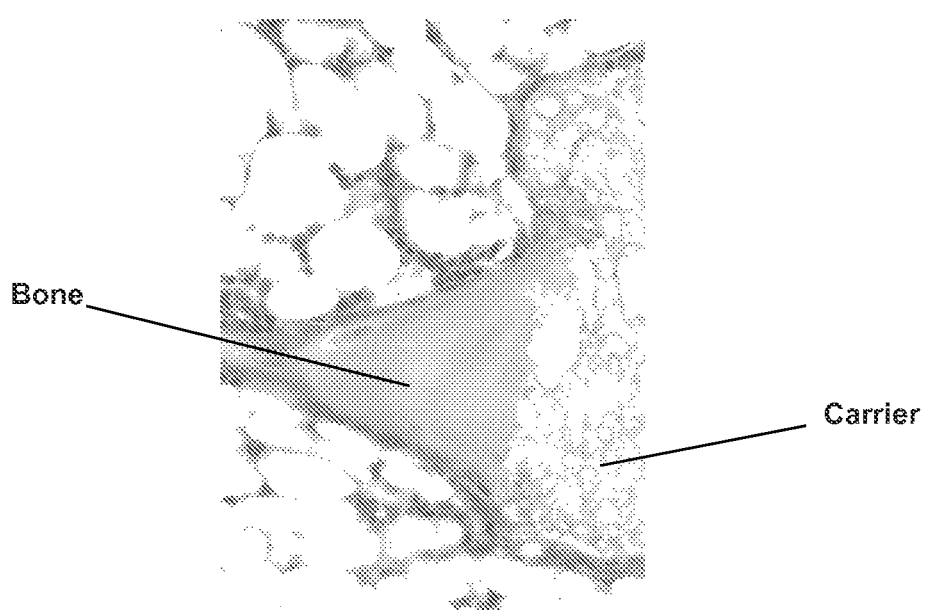
FIG. 6 illustrates the histological appearance of the new bone (Bone) formed on a carrier (Carrier) when bioimplant produced according to the method of the invention was implanted into a mouse.

Backscatter SEM showed that by 28 days bone formed throughout the bioimplant and onto the calcium phosphate particulate that had been incorporated into the PLGA (FIG. 5). Histology confirmed the tissue formed was bone (FIG. 6).

Example 9: An In Vivo Assay for Release of BMPs from Bioimplants

The present example describes how to measure the release of rhBMP-2 from the various bioimplants described in Examples 1, 2, 3, 4 or 5 following implantation into an animal. Methods to do this are well known in the art. For example see Uludag et al. J Biomed Mater Res, 46, 193-202, 1999.

Materials & Methods

Recombinant hBMP-2 is radiolabeled with Iodine125 (I-125) by Perkin Elmer. The radiolabelled rhBMP-2 (hot) is mixed with unlabeled rhBMP-2 (cold) to produce a hot cold mixture of 1:100.

Bioimplants containing known amounts of rhBMP-2 are prepared as in Examples 1 to 5. These bioimplants are then implanted into animals as described in Example 8. At various times the animals are sacrificed and the implant site is dissected out. The dissected tissue is then weighed, and the amount of radioactivity determined using a gamma counter.

To determine whether the counts are associated with protein, the tissue is homogenized in 0.5 ml PBS+0.5% BSA. Two mls of ice cold 10% trichloroacetic acid are added to the homogenate and is then held for at least 1 hour at 4° C. The homogenate is then centrifuged and the supernatant removed. The radioactivity of the precipitate is then measured using a gamma counter.

The radioactivity associated with implants is corrected for the decay and the total amount of BMP remaining in the implant is estimated.

Example 10: Production of a Carrier with a Short Sustained Release Profile

The present example describes means of producing a carrier that releases a growth factor with a short sustained release profile.

Materials & Methods

Macroporous biphasic calcium phosphate (BCP) granules (Eclipse) were purchased from Citagenix (Laval, Qc, Canada.) Recombinant human BMP-2 (rhBMP-2, Induce Biologics Inc) was prepared in formulation buffer (1.5 mg/ml, pH 4.5; 5 mm glutamic acid, 2.5% glycine, 0.5% sucrose and 0.01% Tween™ 80 with $ddH_2O$).

Sterile rhBMP-2 solution was incubated with sterile BCP granules at a ratio of 9.1 µg per 5 mg or 4.55 µg per 5 mg (BMP per BCP) for 15 minutes under shaking. The samples were then frozen and lyophilized aseptically.

Following lyophilization the carriers were weighed into 5 mg aliquots and placed in sterile Eppendorf tubes. Some tubes had 33% F127 (45.5 µl added). The BMP release profile was then determined as described in Example 6.

Results

Figure 7:
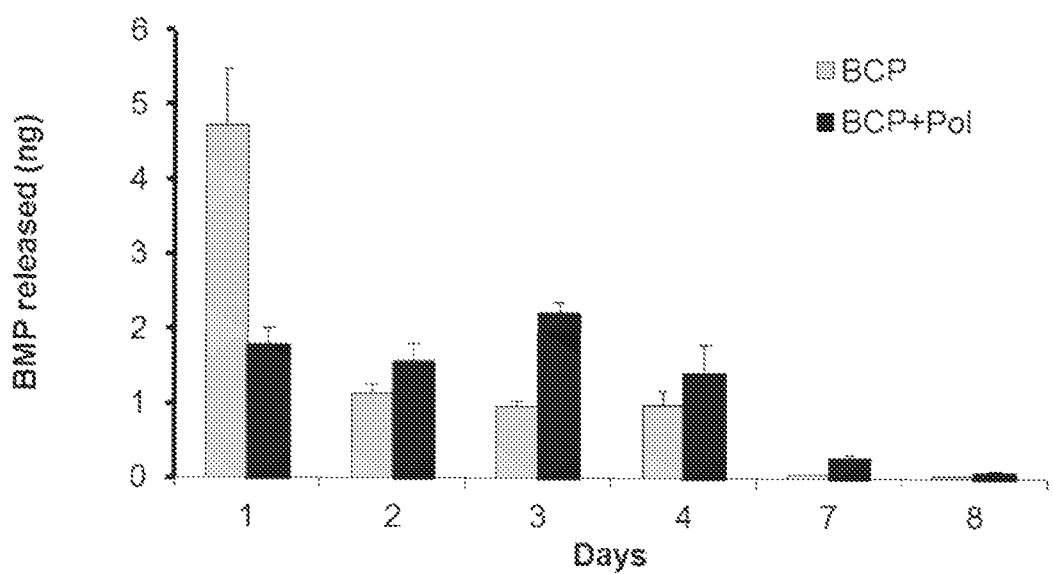
FIG. 7 illustrates a short sustained growth factor release profile produced by a carrier produced according to the method of the invention.

Carriers that were not coated with F127 (BCP) showed a burst release profile with the largest amount of BMP released over the first day and then decreasing amounts of BMP released at each subsequent time point. Mixing the BCP within the F127 (BCP-Pol) resulted in a short sustained release profile where similar amount of BMP were collected each day over the first 4 days (FIG. 7).

Example 11: Altering the Sustained Release Profile of the Carrier

The present example describes a means of altering the release profile from a carrier.

Materials & Methods

PLGA with differing inherent viscosities and molecular weights were purchased from Birmingham Polymers Inc. (Birmingham, Ala.). Carriers were then made using these PLGAs as described in Example 1. The BMP release profile from these carriers was determine according to the method of Example 6.

Results

Figure 8:
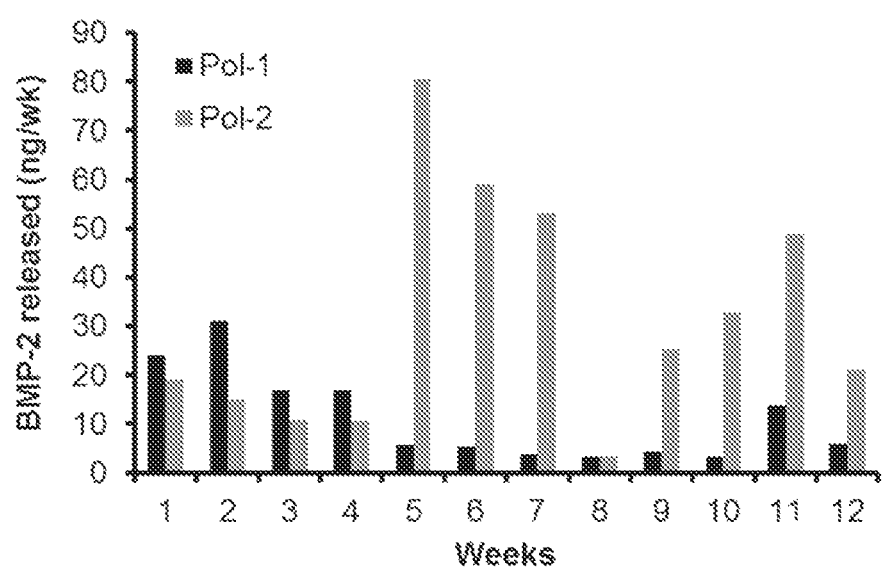
FIG. 8 illustrates how a sustained release profile can be altered by changing the properties of the carrier produced according to the method of the invention.

All carriers produced sustained release profiles. However the amount of BMP released differed depending on the viscosity/molecular weight of the PLGA used. The carriers made with low viscosity PLGA (Pol-1) released more rhBMP-2 than those using the high viscosity (Pol-2) PLGA over the 12 week duration of the study (FIG. 8).

Example 12: Altering Bound and Unbound Protein Distribution During Lyophilization The present example describes a means of altering the distribution of a protein between bound to the carrier particles and unbound lyophilisate by varying the volume of solution lyophilized but keeping total protein and carrier content fixed. This means allows for distribution of protein between carrier-associated and delivery vehicle-associated protein if a delivery vehicle is subsequently added to the lyophilization container.

Materials and Methods

Experimental Design: To test the effect that varying the volume of protein buffer added to the carrier prior to lyophilisation has on the distribution of the lyophilized material, the carrier to liquid protein volume ratio was varied and the total amount of protein (bovine serum albumin, "BSA") and carrier were fixed at 1 mg and 400 mg, respectively.

Based on the criteria above the study was designed as set forth in Table 1, wherein the volume of protein solution added (i.e., 2.0, 1.5, 1.0, 0.75 and 0.5 ml/vial) and the concentration of protein added (i.e., 0.5, 0.67, 1.0, 1.33 and 2.0 mg/ml) were varied.

TABLE 1

Experimental design.

| | Carrier | Volume of Protein solution added (ml/vial) By BSA concentration (mg/ml) | | | | | |
|---|---|---|---|---|---|---|---|
| Gp | mg/vial | 2 | 1.5 | 1.0 | 0.75 | 0.5 | n |
| 1 | 400 | 0.5 | | | | | 3 |
| 2 | 400 | | 0.67 | | | | 3 |
| 3 | 400 | | | 1.0 | | | 3 |
| 4 | 400 | | | | 1.33 | | 3 |
| 5 | 400 | | | | | 2.0 | 3 |

Sample Preparation:

BSA was prepared in formulation buffer (FB) at 2 mg/ml; 1.5 mg/ml; 1 mg/ml; 0.75 mg/ml 0.5 mg/m and 0 mg/ml. 400 mg of carrier was put in each vial containing BSA and FB. Various volumes of protein solution were placed in each vial at the ratios provided in Table 1 and the vials were held at room temperature for 30 minutes. Vials were then frozen and lyophilized. Following lyophilisation, each vial was examined and the appearance of the protein lyophilisate was categorized and photographed (FIG. 9 A-C).

Scoring:

Distribution of protein lyophilisate was scored between 0 and 4, with 0 representing no clear lyophilisate particles visible and 4 representing a clear separation of carrier and protein with a sheet of protein lyophilisate visible.

Protein Measurements:

To quantitate the amount of protein bound to the carrier and the amount lyophilized separately from the granules the lyophilized materials were transferred from the vial to a centrifuge tube and 1 ml of PBS was added to the centrifuge tube and to the vial. The containers were vortexed and rinse solution was collected and centrifuged. The supernatants were assayed for protein content using the Coomassie-Plus protein assay according to the manufacturer's instructions. The amount of bound protein was calculated by subtracting the amounts of protein released from granules and the vial from the amount of protein loaded (1000 µg).

Results

Figure 9A:
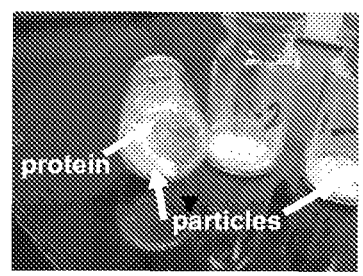
FIGS. 9A-C illustrate lyophilized carriers, wherein the volume of solution lyophilized was varied but the total protein lyophilized was fixed. Treatment groups 1 (FIG. 9A), 3 (FIG. 9B) and 5 (FIG. 9C) are depicted.
Figure 9B:
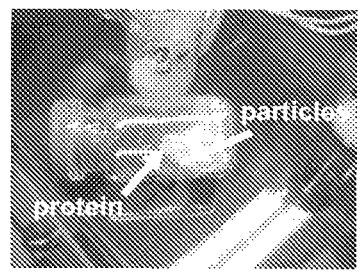
Figure 9C:
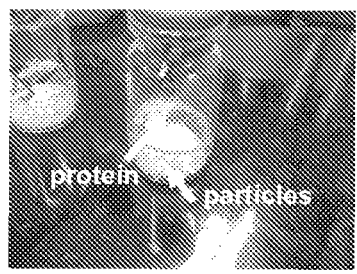

There was a significant difference in distribution of lyophilisate between group 1, which had the lowest protein concentration (i.e., 0.5 mg/ml) and groups 3 (1.0 mg/ml), 4 (1.33 mg/ml) and 5 (2.0 mg/ml)(Table 2). The samples in group 1 had some protein lyophilisate visible on the walls of the vial (FIG. 9A). No lyophilisate was visible between the carrier particles in group 1 samples. In the group 3 samples, some protein lyophilisate was visible on the glass walls of the vial. However, large chunks of protein lyophilisate resembling white or translucent snowflakes were also visible between the carrier particles in group 3 samples (FIG. 9B). In group 5 samples, distinct rims of protein formed on the surface of the glass vial (FIG. 9C). These rims of protein projected chunks of protein lyophilisate. Chunks were also seen lying between the carrier particles in group 5 samples.

TABLE 2

Distribution of protein lyophilisate bound to granules and unbound.

| | Carrier | Volume of Protein solution added (ml/vial) By BSA concentration (mg/ml) | | | | | |
|---|---|---|---|---|---|---|---|
| Gp | mg/vial | 2 | 1.5 | 1.0 | 0.75 | 0.5 | Score |
| 1 | 400 | 0.5 | | | | | 1.0 ± 0.0 |
| 2 | 400 | | 0.67 | | | | 1.7 ± 0.3 |
| 3 | 400 | | | 1.0 | | | 2.2 ± 0.8 |
| 4 | 400 | | | | 1.33 | | 2.3 ± 0.8 |
| 5 | 400 | | | | | 2.0 | 3.0 ± 0.5 |

ANOVA on RANKS P = 0.038

Group 1 vs Group 5, Group 1 vs Group 4 and Group 1 vs Group 3 were all significantly different (Table 2).

Measurement of bound protein indicated there were significant differences between the amounts of bound protein based on the volume of solution added prior to lyophilization. Specifically, the amount of bound protein changed from 68% to 39% when the volume of solution used to deliver 1 mg of protein was changed from 0.5 ml to 2 ml per 400 mg of carrier (Table 3, see bound protein in groups 1 and 5, respectively).

TABLE 3

Protein measurements

| Gp | Released from Granules | Released from Vial | Bound* |
|---|---|---|---|
| 1 | 125 ± 15 | 196 ± 42 | 679 ± 31 |
| 2 | 146 ± 11 | 264 ± 48 | 591 ± 55 |
| 3 | 152 ± 37 | 341 ± 54 | 507 ± 38 |
| 4 | 210 ± 63 | 370 ± 115 | 420 ± 53 |
| 5 | 228 ± 22 | 386 ± 25 | 386 ± 19 |
| ANOVA | P = 0.019 | P = 0.023 | P < 0.001 |

*Bound was calculated by subtracting the amounts of protein released from granules and the vial from the amount loaded (1000 µg).

Post Hoc analysis of the bound protein group indicated that there were significant differences between: group 1 and groups 3, 4, and 5; group 2 and groups 4 and 5; and group 3 and group 5 (Table 4).

TABLE 4

Comparisons for bound protein.
Comparisons for factor:

| Comparison | Diff of Means | t | Unadjusted P | Critical Level | Significant? |
|---|---|---|---|---|---|
| Col 1 vs. Col 5 | 292.423 | 8.666 | 0.00000581 | 0.005 | Yes |
| Col 1 vs. Col 4 | 258.966 | 7.674 | 0.0000169 | 0.006 | Yes |
| Col 2 vs. Col 5 | 204.304 | 6.054 | 0.000123 | 0.006 | Yes |
| Col 1 vs. Col 3 | 171.484 | 5.082 | 0.000477 | 0.007 | Yes |
| Col 2 vs. Col 4 | 170.848 | 5.063 | 0.000490 | 0.009 | Yes |
| Col 3 vs. Col 5 | 120.939 | 3.584 | 0.00498 | 0.010 | Yes |
| Col 1 vs. Col 2 | 88.119 | 2.611 | 0.0260 | 0.013 | No |
| Col 3 vs. Col 4 | 87.483 | 2.592 | 0.0268 | 0.017 | No |
| Col 2 vs. Col 3 | 83.365 | 2.470 | 0.0331 | 0.025 | No |
| Col 4 vs. Col 5 | 33.457 | 0.991 | 0.345 | 0.050 | No |

Example 13: Effect of Varying Carrier and P407 Amount on BMP Release

The present example describes a means for varying the release profile of BMP from the carrier by varying the amount of delivery vehicle and carrier used.

Materials and Methods

Experimental Design:

To test the effect that varying the amount of delivery vehicle and carrier have on the release profile of BMP, the carrier (biphasic calcium phosphate BCP) amount and the delivery vehicle (33% P407 gel) amount were varied in bioimplants wherein the amount of BMP added to the carrier particles was fixed at 40 µg/sample and the BMP was lyophilized onto the carrier granules. The study design is further described in Table 5.

TABLE 5

Study design.

| Amount of Carrier (mg) | Amount of 33% P407 added (µl) | | | |
|---|---|---|---|---|
| | 0 | 30 | 60 | 120 |
| 20 | 3 | 3 | 3 | 3 |
| 40 | 3 | 3 | 3 | 3 |
| 80 | 3 | 3 | 3 | 3 |

Preparation of Materials:

Sterile macroporous BCP granules (0.5-1 mm diameter) comprising 80% β-tricalcium phosphate, 20% Hydroxyapatite were purchased from Citagenix Inc. (Laval, QC). BMP-2 (1 mg/ml) was prepared by Induce Biologics Inc. A 33% poloxamer 407 (P407) gel was prepared by adding 33 g of poloxamer 407 (BASF) to cold water. The solution was then sterilized by autoclaving. The poloxamer gel was kept at 2-8° C. after sterilization.

BMP was lyophilized onto the carriers as follows. The required amount of carrier was weighed out and placed into a sterile Eppendorf tube. The desired amount of BMP-2 was added to the carrier and was held at room temperature for 30 minutes prior to freezing. Once frozen the Eppendorf tubes were placed in a bench top lyophilizer and lyophilized overnight. All procedures were performed aseptically to maintain sterility.

BMP Release:

The lyophilized samples were weighed and placed in Eppendorf tubes to which P407 gel was added and allowed to soak for 20 minutes. Following this, 1 ml of PBS+0.1% BSA was added to each tube which was then placed on a shaker in a 37° C. incubator and gently shaken. At each collection time point (days 1, 2, 3, 4, 7) the tubes were removed, centrifuged and the PBS+BSA removed and fresh PBS+BSA added. The collected PBS+BSA was then stored frozen until analysed.

Analytical Methods:

The amount of BMP released into the solutions was determined using a BMP-2 ELISA (R&D Systems, Minneapolis, Minn.) according to the manufacturer's instructions Statistical Analysis:

The data were tested for normality and equal variance. Normally distributed data with equal variance was tested for significant differences using 2 Way ANOVA (Carrier and P407 were used as the factors). All other data were tested using ANOVA on RANKs. Post-Hoc testing was performed all pairwise using the Student-Newman-Keuls Method. All statistical tests were performed using Sigma Stat v3.5.

Results

The addition of P407 slowed release of BMP for up to 7 days (Table 6). This was a surprising result as P407 gels were previously reported to be effective at slowing drug release for only a matter of hours, after which time it had dispersed into the buffer. The amount of P407 affected BMP release over the first 7 days. From day 4 the amount of P407 initially used determines whether there is a difference between no P407 and +P407 groups (Table 6). The amount of carrier present affected the release of BMP in the presence or absence of P407, from day 2 to 7, with increasing amount of carrier reducing the amount of BMP released (Table 6).

TABLE 6

BMP release over seven days from bioimplants containing
various amounts of P407 gel and BCP particles.

A

| | 20 mg-30 µl P407 | | 20 mg-60 µl P407 | | 20 mg-120 µl P407 | | 20 mg-0 ul P407 | |
|---|---|---|---|---|---|---|---|---|
| | mean | SD | mean | SD | mean | SD | mean | SD |
| Day 1 | 8838 | 1436 | 5718 | 1309 | 4404 | 1260 | 9018 | 7135 |
| Day 2 | 2923 | 1040 | 1282 | 330 | 1884 | 504 | 532 | 152 |
| Day 3 | 1511 | 1043 | 884 | 156 | 1141 | 542 | 674 | 260 |
| Day 4 | 332 | 27 | 443 | 192 | 298 | 54 | 253 | 72 |
| Day 7 | 1004 | 10 | 1301 | 265 | 1085 | 93 | 1028 | 403 |

TABLE 6-continued

BMP release over seven days from bioimplants containing various amounts of P407 gel and BCP particles.

B

| | 40 mg-30 μl P407 | | 40 mg-60 μl P407 | | 40 mg-120 μl P407 | | 40 mg- P407 | |
|---|---|---|---|---|---|---|---|---|
| | mean | SD | mean | SD | mean | SD | mean | SD |
| Day 1 | 4320 | 510 | 4980 | 672 | 6594 | 1152 | 12420 | 1701 |
| Day 2 | 865 | 106 | 999 | 130 | 1362 | 422 | 320 | 119 |
| Day 3 | 409 | 104 | 585 | 393 | 628 | 57 | 220 | 56 |
| Day 4 | 1140 | 151 | 1164 | 173 | 1338 | 81 | 775 | 26 |
| Day 7 | 882 | 201 | 885 | 61 | 949 | 160 | 479 | 44 |

C

| | 80 mg-30 μl P407 | | 80 mg-60 μl P407 | | 80 mg-120 μl P407 | | 80 mg- P407 | |
|---|---|---|---|---|---|---|---|---|
| | mean | SD | mean | SD | mean | SD | mean | SD |
| Day 1 | 6828 | 2359 | 4908 | 660 | 5388 | 1100 | | 2108 |
| Day 2 | 768 | 124 | 862 | 290 | 1288 | 670 | 279.0 | 26 |
| Day 3 | 996 | 113 | 887 | 90 | 918 | 111 | 648.8 | 52 |
| Day 4 | 876 | 205 | 706 | 104 | 844 | 106 | 413.0 | 96 |
| Day 7 | 698 | 67 | 995 | 253 | 843 | 205 | 375.3 | 87 |

TABLE 7

Statistical analysis of BMP release over seven days from bioimplants containing various amounts of P407 gel. 2 Way ANOVA (P values).

| | Dy 1 | Dy 2 | Dy 3 | Dy 4 | Dy 7 | Total |
|---|---|---|---|---|---|---|
| CARRIER | 0.174 | <0.001 | 0.002 | <0.001 | <0.001 | 0.002 |
| P407 | <0.001 | <0.001 | 0.08 | <0.001 | <0.001 | <0.001 |
| SCAFxP407 | 0.015 | 0.006 | 0.642 | 0.19 | 0.283 | <0.001 |

Day one data showed that there was significantly more BMP released from the carrier in the absence of P407 than when it was present (Table 8).

While the amount of carrier alone was not considered to impact BMP release on day 1 there was an interaction between carrier amount and P407 amount. Specifically 20 mg of carrier the amount of P407 gel used significantly influenced BMP released (30 v 120 and 30 v 60) while in samples with 40 or 80 mg of carrier this was not observed (Table 8).

TABLE 8

ANOVA table for day one results.

| Comparison | Diff of Means | t | Unadjusted P | Critical Level | Significant? |
|---|---|---|---|---|---|
| Comparisons for factor: P407 within 20 mg carrier group | | | | | |
| 0.000 vs. 120.000 | 8718.000 | 7.829 | 0.000 | 0.009 | Yes |
| 0.000 vs. 60.000 | 7404.000 | 6.649 | 0.000 | 0.010 | Yes |
| 30.000 vs. 120.000 | 4434.000 | 3.982 | 0.001 | 0.013 | Yes |
| 0.000 vs. 30.000 | 4284.000 | 3.847 | 0.001 | 0.017 | Yes |
| 30.000 vs. 60.000 | 3120.000 | 2.802 | 0.010 | 0.025 | Yes |
| 60.000 vs. 120.000 | 1314.000 | 1.180 | 0.250 | 0.050 | No |
| Comparisons for factor: P407 within 40 mg carrier group | | | | | |
| 0.000 vs. 30.000 | 8100.000 | 7.274 | 0.000 | 0.009 | Yes |
| 0.000 vs. 60.000 | 7440.000 | 6.681 | 0.000 | 0.010 | Yes |
| 0.000 vs. 120.000 | 5826.000 | 5.232 | 0.000 | 0.013 | Yes |
| 120.000 vs. 30.000 | 2274.000 | 2.042 | 0.052 | 0.017 | No |
| 120.000 vs. 60.000 | 1614.000 | 1.449 | 0.160 | 0.025 | No |
| 60.000 vs. 30.000 | 660.000 | 0.593 | 0.559 | 0.050 | No |

TABLE 8-continued

ANOVA table for day one results.

| Comparison | Diff of Means | t | Unadjusted P | Critical Level | Significant? |
|---|---|---|---|---|---|
| Comparisons for factor: P407 within 80 mg carrier group | | | | | |
| 0.000 vs. 60.000 | 6330.000 | 5.684 | 0.000 | 0.009 | Yes |
| 0.000 vs. 120.000 | 5850.000 | 5.253 | 0.000 | 0.010 | Yes |
| 0.000 vs. 30.000 | 4410.000 | 3.960 | 0.001 | 0.013 | Yes |
| 30.000 vs. 60.000 | 1920.000 | 1.724 | 0.098 | 0.017 | No |
| 30.000 vs. 120.000 | 1440.000 | 1.293 | 0.208 | 0.025 | No |
| 120.000 vs. 60.000 | 480.000 | 0.431 | 0.670 | 0.050 | No |

Day two data showed that both carrier amount and P407 amount significantly impacted the BMP release, with interactions occurring (Table 9). The amount of P407 needed for effect was dependant on the amount of carrier.

TABLE 9

ANOVA table for day two results.

| Comparison | Diff of Means | t | Unadjusted P | Critical Level | Significant? |
|---|---|---|---|---|---|
| Comparisons for factor: P407 within 20 | | | | | |
| 30.000 vs. 0.000 | 2391.000 | 6.785 | 0.000 | 0.009 | Yes |
| 30.000 vs. 60.000 | 1640.400 | 4.655 | 0.000 | 0.010 | Yes |
| 120.000 vs. 0.000 | 1352.400 | 3.838 | 0.001 | 0.013 | Yes |
| 30.000 vs. 120.000 | 1038.600 | 2.947 | 0.007 | 0.017 | Yes |
| 60.000 vs. 0.000 | 750.600 | 2.130 | 0.044 | 0.025 | No |
| 120.000 vs. 60.000 | 601.800 | 1.708 | 0.101 | 0.050 | No |
| Comparisons for factor: P407 within 40 | | | | | |
| 120.000 vs. 0.000 | 1042.200 | 2.957 | 0.007 | 0.009 | Yes |
| 60.000 vs. 0.000 | 679.800 | 1.929 | 0.066 | 0.010 | No |
| 30.000 vs. 0.000 | 545.400 | 1.548 | 0.135 | 0.013 | No |
| 120.000 vs. 30.000 | 496.800 | 1.410 | 0.171 | 0.017 | No |
| 120.000 vs. 60.000 | 362.400 | 1.028 | 0.314 | 0.025 | No |
| 60.000 vs. 30.000 | 134.400 | 0.381 | 0.706 | 0.050 | No |
| Comparisons for factor: P407 within 80 | | | | | |
| 120.000 vs. 0.000 | 1009.200 | 2.864 | 0.009 | 0.009 | No |
| 60.000 vs. 0.000 | 582.600 | 1.653 | 0.111 | 0.010 | No |

TABLE 9-continued

ANOVA table for day two results.

| Comparison | Diff of Means | t | Unadjusted P | Critical Level | Significant? |
|---|---|---|---|---|---|
| 120.000 vs. 30.000 | 520.200 | 1.476 | 0.153 | 0.013 | No |
| 30.000 vs. 0.000 | 489.000 | 1.388 | 0.178 | 0.017 | No |
| 120.000 vs. 60.000 | 426.600 | 1.211 | 0.238 | 0.025 | No |
| 60.000 vs. 30.000 | 93.600 | 0.266 | 0.793 | 0.050 | No |
| Comparisons for factor: SCAF within 30 | | | | | |
| 20.000 vs. 80.000 | 2154.600 | 6.114 | 0.000 | 0.017 | Yes |
| 20.000 vs. 40.000 | 2057.400 | 5.838 | 0.000 | 0.025 | Yes |
| 40.000 vs. 80.000 | 97.200 | 0.276 | 0.785 | 0.050 | No |

Day three results indicated that the amount of carrier was the primary factor that affected BMP release. However P407 gel amount neared significance in several groups (Table 10).

TABLE 10

ANOVA table for day three results

| Comparison | Diff of Means | t | Unadjusted P | Critical Level | Significant? |
|---|---|---|---|---|---|
| Comparisons for factor: CARRIER | | | | | |
| 20.000 vs. 40.000 | 592.200 | 3.876 | 0.000720 | 0.017 | Yes |
| 80.000 vs. 40.000 | 402.090 | 2.632 | 0.0146 | 0.025 | Yes |
| 20.000 vs. 80.000 | 190.110 | 1.244 | 0.225 | 0.050 | No |
| Comparisons for factor: P407 | | | | | |
| 30.000 vs. 0.000 | 457.820 | 2.595 | 0.0159 | 0.009 | No |
| 120.000 vs. 0.000 | 381.140 | 2.161 | 0.0409 | 0.010 | No |
| 60.000 vs. 0.000 | 270.840 | 1.535 | 0.138 | 0.013 | No |
| 30.000 vs. 60.000 | 186.980 | 1.060 | 0.300 | 0.017 | No |
| 120.000 vs. 60.000 | 110.300 | 0.625 | 0.538 | 0.025 | No |
| 30.000 vs. 120.000 | 76.680 | 0.435 | 0.668 | 0.050 | No |

Day four results indicated that both the amount of carrier and P407 gel affected BMP release, although there appeared to be no interaction between the two (Table 11). There were no differences in the amount of P407 gel, as long as more than 30 µl of gel had been used. BMP release differed between all 3 amounts of carrier used (Table 11).

TABLE 11

ANOVA table for day four results.

| Comparison | Diff of Means | t | Unadjusted P | Critical Level | Significant? |
|---|---|---|---|---|---|
| Comparisons for factor: CARRIER | | | | | |
| 40.000 vs. 20.000 | 772.380 | 15.479 | 5.465E−014 | 0.017 | Yes |
| 40.000 vs. 80.000 | 394.380 | 7.904 | 0.0000000391 | 0.025 | Yes |
| 80.000 vs. 20.000 | 378.000 | 7.575 | 0.0000000817 | 0.050 | Yes |
| Comparisons for factor: P407 | | | | | |
| 120.000 vs. 0.000 | 346.440 | 6.013 | 0.00000330 | 0.009 | Yes |
| 30.000 vs. 0.000 | 302.820 | 5.256 | 0.0000218 | 0.010 | Yes |
| 60.000 vs. 0.000 | 290.780 | 5.047 | 0.0000369 | 0.013 | Yes |
| 120.000 vs. 60.000 | 55.660 | 0.966 | 0.344 | 0.017 | No |
| 120.000 vs. 30.000 | 43.620 | 0.757 | 0.456 | 0.025 | No |
| 30.000 vs. 60.000 | 12.040 | 0.209 | 0.836 | 0.050 | No |

Day seven results were similar to day 4 results with both the amount of carrier particles and P407 gel affecting BMP release (Table 12). At this time however a minimum amount of 60 µl of P407 gel per implant must be used.

TABLE 12

ANOVA table for day seven results.

| Comparison | Diff of Means | t | Unadjusted P | Critical Level | Significant? |
|---|---|---|---|---|---|
| Comparisons for factor: CARRIER | | | | | |
| 20.000 vs. 80.000 | 376.455 | 4.868 | 0.0000581 | 0.017 | Yes |
| 20.000 vs. 40.000 | 305.310 | 3.948 | 0.000601 | 0.025 | Yes |
| 40.000 vs. 80.000 | 71.145 | 0.920 | 0.367 | 0.050 | No |
| Comparisons for factor: P407 | | | | | |
| 60.000 vs. 0.000 | 432.820 | 4.847 | 0.0000613 | 0.009 | Yes |
| 120.000 vs. 0.000 | 331.420 | 3.712 | 0.00109 | 0.010 | Yes |
| 30.000 vs. 0.000 | 233.820 | 2.619 | 0.0151 | 0.013 | No |
| 60.000 vs. 30.000 | 199.000 | 2.229 | 0.0355 | 0.017 | No |
| 60.000 vs. 120.000 | 101.400 | 1.136 | 0.267 | 0.025 | No |
| 120.000 vs. 30.000 | 97.600 | 1.093 | 0.285 | 0.050 | No |

Discussion

Taken together, these results show that it is possible to vary the release profile of BMP by varying the amount of P407 and carrier used. These results also show that, in contrast to previous reports of using P407 for drug delivery over a period of a few hours, the use of P407 gel in combination with carrier results in inhibition of protein release for up to 7 days. It is contemplated herein that, after the majority of the P407 has dissolved in the first several hours, a thin layer of P407 gel might remain on the surface of the carrier, slowing the rate of protein release.

Example 14: Evaluation of In Vitro Protein Release from Different Carrier Particles The present example describes bioimplants comprising calcium sulphate dehydrate (CSD) particles onto which rhBMP-2 was lyophilized. These bioimplants produced a larger and more consistent release of BMP over 14 days relative to bioimplants comprising 2 types of calcium phosphate particles as the carrier.

Materials and Methods

Experimental Design:

Three carriers were tested: calcium sulphate dihydrate (CSD), hydroxyapatite (HAp) and biphasic calcium phosphate (BCP) in bioimplants, wherein the ratio of BMP to carrier was 40 µg:20 mg, the ratio of carrier to delivery vehicle (i.e., P407) was 200 µl:20 mg and wherein the BMP was lyophilized onto carrier granules. Experimental design is further set forth in Table 13.

TABLE 13

Carrier Comparison.

| Group | Carrier | N |
|---|---|---|
| CSD(B) + P407 | Calcium sulphate | 4 |
| HAp(B) + P407 | Hydroxyapatite | 4 |
| BCP(B) + P407 | Biphasic Calcium phosphate | 4 |

Preparation of Materials:

Sterile macroporous BCP granules (0.5-1 mm diameter) comprising 80% β-tricalcium phosphate, 20% Hydroxyapatite were purchased from Citagenix Inc. (Laval, QC). Sterile CSD granules (0.5-1.2 mm) were prepared by grinding Osteoset pellets (Wright Medical Technology Canada Ltd., Mississauga, ON) and sieving between 1.18 mm and 0.5 mm sieves. Sterile hydroxyapatite granules were obtained from Tissue Regeneration Therapeutics (Toronto, ON). BMP-2 (1 mg/ml) was prepared by Induce Biologics Inc. A 33% poloxamer 407 (P407) gel was prepared by adding 33 g of poloxamer 407 (BASF) to cold water. The solution was then sterilized by autoclaving. The poloxamer gel was kept at 2-8° C. after sterilization.

BMP Lyophilization onto Carrier Particles:

The required amount of carrier was weighed out and placed into a sterile Eppendorf tube. The desired amount of BMP-2 was added to the carrier and was held at room temperature for 30 minutes prior to freezing. Once frozen, the Eppendorf tubes were placed in a bench top lyophilizer and lyophilized overnight. All procedures were performed aseptically to maintain sterility.

BMP Release In Vitro:

80 µl of P407 gel was added to the carrier and associated rhBMP-2 and allowed to soak for 20 minutes. Following this, 1 ml of PBS+0.1% BSA was added to each tube which was then placed on a shaker in a 37° C. incubator and gently shaken. At each collection time point (days 1, 2, 3, 4, 7, 10 and 14) the tubes were removed, centrifuged and the PBS+BSA removed and fresh PBS+BSA added. Collected PBS+BSA was then stored frozen until analysed.

Analytical Methods:

The amount of BMP released into the solutions was determined using a BMP-2 ELISA (R&D Systems, Minneapolis, Minn.) according to the manufacturer's instructions.

Statistical Analysis:

The data were tested for normality and equal variance. Normally distributed data with equal variance were tested for significant differences using ANOVA. All other data were tested using ANOVA on RANKs. Post-Hoc testing was performed all pairwise using the Student-Newman-Keuls Method. All statistical tests were performed using Sigma Stat v3.5.

Results

Post-Hoc testing indicated that the calcium sulphate carrier particles released more BMP than the BCP carrier particles at all time points tested (Table 14). The CSD carrier particles also released more BMP than the Hap carrier particles at day 1, day 2 and day 7. BMP release from the HAp carrier particles differed from BCP on days 7 and 10.

TABLE 14

BMP release from various carrier particles.

| Day | Calcium sulphate (CSD) | Hydroxyapatite (HAp) | Biphasic Calcium phosphate (BCP) | P ANOVA |
|---|---|---|---|---|
| 1 | 1863 ± 231 | 138 ± 34 | 673 ± 608 | 0.004 |
| 2 | 910 ± 171 | 218 ± 88 | 400 ± 165 | 0.003 |
| 3 | 1457 ± 650 | 1363 ± 289 | 690 ± 421 | 0.181 |
| 4 | 1200 ± 1381 | 1070 ± 46 | 344* | not done |
| 7 | 744 ± 124 | 397 ± 73 | 172 ± 50 | <0.001 |
| 10 | 373 ± 254 | 199 ± 35 | 109 ± 19 | 0.011 |
| 14 | 232 ± 58 | 150 ± 30 | 97 ± 2 | 0.013 |
| total | 6780 ± 2431 | 3536 ± 438 | 2486 ± 916 | 0.032 |

*only a single sample was measured, consequently the ANOVA was not performed at this time point.

Discussion

These results show that the CSD carrier particles released more BMP-2 than the other carrier particles tested in total over 14 days and at all but the 3 day timepoint.

Example 15: Production of a BMP Carrier Having Improved Potency In Vivo Relative to Known Carriers Used in Multiphasic BMP Bioimplant The present example describes the evaluation of various carrier components to determine which produces the most bone when used as part of a multiphasic BMP bioimplant. In this example "improved bone growth" or "improved capacity for boney ossicle formation" refers to an increase in the size and/or density of bone ossicles relative to that of known carriers comprising the same BMP. The results of this study show that bioimplants using CSD particles, onto which rhBMP-2 was lyophilized produced larger ossicles of bone when implanted than bioimplants containing hydroxyapatite or biphasic calcium phosphate carriers.

Materials and Methods

Experimental Design:

To identify a carrier with relatively high bone producing capacity calcium sulphate dihydrate (CSD), hydroxyapatite (HAp) and biphasic calcium phosphate (BCP) were tested in bioimplants wherein the ratio of BMP to implant volume was fixes at 40 µg:20 mg, the ratio of carrier to delivery vehicle (i.e., P407) was fixed at 200 µl:20 mg and the BMP was lyophilized onto carrier granules. Experimental design is further set forth in Table 15.

TABLE 15

Carrier Comparison

| Gp | Carrier | N |
|---|---|---|
| CSD(B) + P407 | Calcium sulphate | 8 |
| HAp(B) + P407 | Hydroxyapatite | 8 |
| BCP(B) + P407 | Biphasic Calcium phosphate | 8 |

Preparation of Materials:

Sterile macroporous BCP granules (0.5-1 mm diameter) comprising 80% β-tricalcium phosphate, 20% Hydroxyapatite were purchased from Citagenix Inc. (Laval, QC). Sterile CSD granules (0.5-1.2 mm) were prepared by grinding Osteoset pellets (Wright Medical Technology Canada Ltd., Mississauga, ON) and sieved between 1.18 mm and 0.5 mm sieves. Sterile hydroxyapatite granules were obtained from Tissue Regeneration Therapeutics (Toronto, ON). BMP-2 (1 mg/ml) was prepared by Induce Biologics Inc. A 33% poloxamer 407 (P407) gel was prepared by adding 33 g of poloxamer 407 (BASF) to cold water. The solution was then sterilized by autoclaving. The poloxamer gel was kept at 2-8° C. after sterilization. BMP was lyophilized onto the carriers as follows: the required amount of carrier was weighed out and placed into a sterile Eppendorf tube. The desired amount of BMP-2 was added to the carrier and was held at room temperature for 30 minutes prior to freezing. Once frozen the Eppendorf tubes were placed in a bench top lyophilizer and lyophilized overnight. All procedures were performed aseptically to maintain sterility.

Surgical Model:

The osteoinductivity of the various bioimplants was evaluated in the mouse muscle pouch assay (Barr et al. Oral Surg Oral Med Oral Pathol Oral Radiol Endod. 2010; 109(4):531-40).

Samples where poloxamer was to be mixed with carrier were prepared by pouring the carrier granules onto a sterile stainless steel tray. The poloxamer was kept on ice and the appropriate amount of poloxamer gel was applied by pipette to the carrier granules. The carrier and gel were mixed and then carefully placed into a gelatin capsule which was then placed in the muscle pouch.

Male IGS mice (approximately 22 gm) had intramuscular pouches formed in their biceps femoris muscle by blunt dissection. The bioimplant was then placed into the pouch. The skin was then pulled together and closed using Michel clips.

The mice were monitored daily. Originally the mice were to be euthanized after 28 days. However due to some implants forming so much bone that bridging occurred between the spine and the femur, which restricted the mice's mobility, all mice were sacrificed after 18 days. Following sacrifice of the animals, the rear limbs were dissected out and fixed using neutral buffered formalin.

Analytical Methods:

The amount of bone formed by the bioimplants was determined by micro CT. Appropriate values were adjusted for the presence of calcium from the residual carrier as previously described (Humber et al. Oral Surg. Oral Med Oral Pathol. Oral Radiol. Endod. 2010 March; 109(3):372-84). Briefly, the region where the implant had been placed was imaged using a General Electric Healthcare eXplore™ Locus SP microCT scanner. The residual carrier and any new mass that had formed around the implant in the muscle (collectively called an ossicle) was outlined every 10 slices to define the region of interest (ROI).

Carrier material was denser than the new bone. Therefor it was possible to determine threshold values for new bone and carrier separately by imaging multiple samples from each group and taking an average of the grey-scale values. For the purpose of standardization, the lowest carrier threshold value obtained for a material (i.e., CSD) was used for all carriers (i.e., 1835). Similarly, a single value for new bone was used (i.e., 555).

Analyses were performed using the 2 threshold values (i.e., 1835 and 555). The upper threshold distinguished carrier from bone and soft tissue, while the lower distinguished bone+carrier from soft tissue. By subtracting the upper threshold values from the lower threshold values the values for bone only were determined. Seven different parameters were measured using the microCT. Table 16 describes the parameters obtained directly from the microCT and any thresholding that impacted the result. Table 17 describes the derived parameters and how they are calculated.

TABLE 16

Reported parameters provided by microCT.

| Parameter | Abbreviation | Description | Threshold Dependent |
|---|---|---|---|
| Total Volume | TV | Total volume of ROI. Includes volume occupied by bone, carrier and soft tissues | No |
| Bone Volume | BV (SV) | Volume occupied by voxels with grey scale above threshold value in the ROI When using the upper threshold this would represent the carrier volume When using the lower threshold this would be a measure of the bone + carrier volume | Yes |
| Bone Mineral Content | BMC | Mineral content within the ROI. This is based on comparison of greyscale of all voxels in | No |
| Bone Mineral Density | BMD | BMC/TV | No |
| Tissue Mineral Content | TMC (uTMC) | Mineral content of tissue within the ROI with voxels greater than the threshold value (i.e. bone) When using the upper threshold this would represent the mineral content due to the carrier | Yes |
| Tissue Mineral Density | TMD (uTMD) | TMC/BV When using the upper threshold this would represent the mineral density of the carrier | Yes |
| Bone Volume Fraction | BVF (SVF) | BV/TV The fraction of the total volume occupied by tissue with a grey scale greater than the threshold value When using the upper threshold this would represent the percentage of the ossicle occupied by carrier | Yes |

TABLE 17

Calculated parameters (Lower threshold-upper threshold).

| Parameter | Abbreviation | How calculated | Threshold Dependant |
|---|---|---|---|
| Adjusted Bone Volume | aBV | BV − SV | Yes |
| Adjusted Tissue Mineral Content | aTMC | TMC − uTMC | Yes |
| Adjusted Tissue Mineral Density | aTMD | aTMC/aBV | Yes |
| Adjusted Bone Volume Fraction | aBVF | aBV/TV | Yes |

The two measures used to determine osteoinductive activity were total volume (TV) and adjusted bone volume (aBV).

Histology:

Following micro CT analysis, samples were decalcified and processed for light microscopy.

Statistical Analysis:

MicroCT parameters were tested for normality and equal variance. Normally distributed data with equal variance was tested for significant differences using ANOVA. All other data was tested using ANOVA on RANKs. Post-Hoc testing was performed all pairwise using the Student-Newman-Keuls Method. All statistical tests were performed using Sigma Stat v3.5.

Results

Comparison of Carriers: MicroCT results indicated that CSD carriers produced larger ossicles than either of the calcium phosphate based carriers by total volume (Table 18). There was also a trend for the CSD ossicles to contain more new bone than either of the calcium phosphate containing carriers (Table 19).

TABLE 18

Total Volume (mm³)

| Gp | Carrier | mean | sd |
|---|---|---|---|
| CSD(B) + P407 | Calcium sulphate | 209 | 70 |
| HAp(B) + P407 | Hydroxyapatite | 135 | 28 |
| BCP(B) + P407 | Biphasic Calcium phosphate | 158 | 22 |
| P(ANOVA on RANKS) | | 0.017 | |

Post Hoc Test:

All pairwise multiple comparison procedures (Student-Newman-Keuls Method). CSD vs HAp (P<0.05); CSD vs BCP (P<0.05); HAp vs BCP (no significant difference).

TABLE 19

Adjusted Bone Volume (mm³)

| Gp | Carrier | Mean | sd |
|---|---|---|---|
| CSD(B) + P407 | Calcium sulphate | 98.1 | 41.2 |
| HAp(B) + P407 | Hydroxyapatite | 67.8 | 14.1 |
| BCP(B) + P407 | Biphasic Calcium phosphate | 77.5 | 17.8 |
| | P(ANOVA on RANKS) | 0.12 | |

Histology:

Histological evaluation indicated that for all bioimplants the ossicles primarily comprised a shell of bone surrounding a mixture of bone, cartilage and marrow tissue. There were no signs of inflammation in any of the implants.

Residual calcium phosphate granules were visible in the bioimplants containing BCP, or HAp while CSD appears to be rapidly resorbed with only a few CAS granules seen.

These results show that when BMP-2 was lyophilized onto CSD carriers the CSD-P407 bioimplant produced larger bone ossicles containing more bone than the other carriers onto which BMP-2 was lyophilized.

Example 16: Production of a Bioimplant Having Increased Potency by Distributing the BMP Both onto the Carrier and into the Delivery Vehicle Compared to Bioimplants where the BMP was Only on the Carrier The present example describes the evaluation of calcium sulphate and calcium phosphate individually and as a mixture, as carriers of BMP that might improve bone production relative to ACS in mouse muscle pouch assays, wherein a preferred ratio of BMP on carrier relative to the delivery vehicle (i.e. P407) and a preferred ratio of calcium sulphate to biphasic calcium phosphate is determined.

Materials and Methods

Experimental Design: To identify a carrier with relatively high bone producing capacity mixtures of calcium sulphate dehydrate (CSD) and biphasic calcium phosphate (BCP) in the ratios of 1:0, 3:1, 1:1 and 0:1 were tested. Further, the ratio of BMP on carrier versus in the F127 delivery vehicle was varied such that ratios of 100:0, 90:10 and 70:30 CSD:BCP were tested. Each variable was tested in a bioimplant wherein the ratio of BMP to implant volume was 40 µg:~50 µl, based on a goal of <1 mg/cc and wherein the ratio of carrier to F127 was 30:45. Experimental design is further set forth in Table 20.

TABLE 20

Experimental design.

| Gp (side a/b) | Name | CSD (mg) | BCP (mg) | F127 (µl) | BMP (µg) | CARRIER/ P407 BMP ratio | n |
|---|---|---|---|---|---|---|---|
| 1a | ACS(B) (Infuse) | | | | 80 | soak | 12 |
| 1b | ACS | | | | 0 | — | |
| 2a | CSD(B) + F | 30 | — | 45 | 40 | 100/0 | 12 |
| 2b | CSD + F | 30 | | 45 | 0 | — | |
| 3a | CSD(B) + F(B) | 30 | | 45 | 40 | 70/30 | 12 |
| 4a | BCP(B) + F(B) | | 30 | 45 | 40 | 70/30 | 12 |
| 4b | BCP + F | | 30 | 45 | 0 | — | |
| 5a | 2:1CSD(B)BCP(B) + F(B) | 20 | 10 | 45 | 40 | 70/30 | 12 |
| 5b | 2:1CSD-BCP + F | 20 | 10 | 45 | 0 | — | |
| 6a | 2:1CSD(B)BCP(B) + F(B) | 20 | 10 | 45 | 40 | 90/10 | 12 |
| 7a | 1:1CSD(B)BCP(B) + F(B) | 15 | 15 | 45 | 40 | 70/30 | 12 |
| 7b | 1:1CSD-BCP + F | | | 45 | 0 | — | |
| 8a | 1:1CSD(B)BCP(B) + F(B) | 15 | 15 | 45 | 40 | 90/10 | 12 |

Preparation of Materials:

Sterile macroporous BCP granules (0.5-1 mm diameter) comprising 80% β-tricalcium phosphate, 20% Hydroxyapatite were purchased from Citagenix Inc. (Laval, QC). Sterile CSD granules (0.5-1.2 mm) were prepared by grinding Osteoset pellets (Wright Medical Technology Canada Ltd., Mississauga, ON) and sieving between 1.18 mm and 0.5 mm sieves.

The Infuse® kit was purchased from Medtronic of Canada Ltd. Infuse BMP-2 was prepared by adding water for injection to the lyophilized rhBMP-2 powder in the Infuse® kit. The ACS sponge was cut into pieces of approximate 5×5 mm and placed in Eppendorf capsules.

Induce BMP-2 (1 mg/ml) was prepared by Induce Biologics Inc. A 33% poloxamer 407 (P407) gel was prepared by adding 33 g of poloxamer 407 (BASF) to cold water. The solution was then sterilized by autoclaving. The poloxamer gel was kept at 2-8° C. after sterilization.

BMP was lyophilized onto the carriers as follows: The required amount of carrier was weighed out and placed into a sterile Eppendorf tube. The desired amount of BMP-2 was added to the carrier and was held at room temperature for 30 minutes prior to freezing. Once frozen the Eppendorf tubes were placed in a bench top lyophilizer and lyophilized overnight. All procedures were performed aseptically to maintain sterility. BMP-P407 samples were prepared in bulk in sterile Eppendorf tubes by adding BMP-2 to BMP at the desired concentration. At the time of surgery the appropriate amount of P407 was pipetted out of the tube.

Surgical Model:

As set forth in Example 15.

Analytical methods: Micro CT and histology analyses were as set forth in Example 15.

Statistical Analysis:

As the ACS alone did not form ossicles that could be measured they were not included in any statistical analyses. The microCT parameters were tested for normality and equal variance. Normally distributed data with equal variance was tested for significant differences using ANOVA. All other data was tested using ANOVA on RANKs. Post-Hoc testing was performed all pairwise using the Student-Newman-Keuls Method. All statistical tests were performed using Sigma Stat v3.5.

Results

Effect of Distributing BMP between the carrier granules and the P407 gel: When BMP was distributed between the P407 gel and the CSD granules it produced larger ossicles than when all of the BMP was lyophilized onto the CSD (total bone volume). (Group3a>Group2a) (Table 22).

When using the 2:1 CSD-BCP granules more bone was formed when 70% was lyophilized onto the granules and 30% was in the P407 gel then when 90% was lyophilized and 10% was in the gel (total bone volume). (Group5a>Group7a) (Table 22).

Effect of Using CSD Rather than BCP Granules:

In groups with the same distribution of BMP between the granules and P407 we found that using CSD granules produced larger ossicles than BCP (total bone volume) (Gp 3a>Gp 4a) (Table 20). When CDS was mixed with BCP groups with more than 50% CSD in the ratio formed the larger ossicles (Group3a (100CSD)>5a (67% CSD)>Group 7a (50% CSD)=4a (0% CSD) (total bone volume) (Table 22).

TABLE 21

MicroCT; total volume of bone produced.

| Group | Name | CARRIER/F127 BMP ratio | Mean | SD |
|---|---|---|---|---|
| 1a | ACS(B) (Infuse) | soak | 200.6 | 94.1 |
| 1b | ACS | | | |
| 2a | CSD(B) + F | 100/0 | 270.7 | 52.2 |
| 2b | CSD + F | — | 164.6 | 57.9 |
| 3a | CSD(B) + F(B) | 70/30 | 384.6 | 68.1 |
| 4a | BCP(B) + F(B) | 70/30 | 299.1 | 104.3 |
| 4b | BCP + F | — | 90.6 | 81.1 |
| 5a | 2:1CSD(B)BCP(B) + F(B) | 70/30 | 336.5 | 125.8 |
| 5b | 2:1CSD-BCP + F | — | 121.2 | 81.6 |
| 6a | 2:1CSD(B)BCP(B) + F(B) | 90/10 | 259.2 | 45.1 |
| 7a | 1:1CSD(B)BCP(B) + F(B) | 70/30 | 275.6 | 97.1 |
| 7b | 1:1CSD-BCP + F | — | 137.9 | 53.5 |
| 8a | 1:1CSD(B)BCP(B) + F(B) | 90/10 | 269.7 | 53.9 |
| | P value (ANOVA on RANKS) | | <0.001 | |

TABLE 22

Post Hoc Test (comparison of BMP containing groups in total volume analysis). All Pairwise Multiple Comparison Procedures (Student-Newman-Keuls Method).

| Comparison | Diff of Ranks | q | P < 0.05 |
|---|---|---|---|
| 3a-TV vs 1aTV | 811.000 | 8.404 | Yes |
| 3a-TV vs 6a-TV | 510.000 | 6.036 | Yes |
| 3a-TV vs 7a-TV | 491.000 | 6.773 | Yes |
| 3a-TV vs 8a-TV | 451.000 | 7.455 | Yes |
| 3a-TV vs 2aTV | 436.000 | 8.990 | Yes |
| 3a-TV vs 4a-TV | 396.500 | 10.864 | Yes |
| 3a-TV vs 5a-TV | 203.000 | 8.287 | Yes |
| 5a-TV vs 1aTV | 608.000 | 7.195 | Yes |
| 5a-TV vs 6a-TV | 307.000 | 4.235 | Yes |
| 5a-TV vs 7a-TV | 288.000 | 4.760 | Yes |
| 5a-TV vs 8a-TV | 248.000 | 5.114 | Yes |
| 5a-TV vs 2aTV | 233.000 | 6.384 | Yes |
| 5a-TV vs 4a-TV | 193.500 | 7.900 | Yes |
| 2aTV vs 1aTV | 375.000 | 6.199 | Yes |
| 4a-TV vs 1aTV | 414.500 | 5.717 | Yes |
| 6a-TV vs 1aTV | 301.000 | 12.288 | Yes |
| 7a-TV vs 1aTV | 320.000 | 8.768 | Yes |
| 8a-TV vs 1aTV | 360.000 | 7.423 | Yes |

Effect of Distributing BMP Between the Granules and the P407 Gel:

When BMP was distributed between the P407 gel and the CSD granules it produced more bone than when all of the BMP was lyophilized onto the CSD (adjusted bone volume). (Gp3a>Gp2a) (Table 24).

Effect of Using CSD Rather than BCP Granules:

In groups with the same distribution of BMP between the granules and P407 we found that using CSD granules produced larger ossicles than BCP (adjusted bone volume) (Gp 3a>Gp 4a) (Table 24). When CDS was mixed with BCP groups with more than 50% CSD in the ratio formed the larger ossicles (adjusted bone volume) (Gp3a (100CSD)>5a (67% CSD)>4a (0% CSD) (Table 24).

TABLE 23

Adjusted Bone Volume (aBV). All pairwise multiple comparison procedures (Student-Newman-Keuls Method).

| Group | Name | CARRIER/F127 BMP ratio | Mean | SD |
|---|---|---|---|---|
| 1a | ACS(B) (Infuse) | soak | 75.4 | 62.6 |
| 1b | ACS | | | |
| 2a | CSD(B) + F | 100/0 | 115.4 | 34.0 |
| 2b | CSD + F | — | 68.8 | 27.4 |
| 3a | CSD(B) + F(B) | 70/30 | 163.3 | 39.0 |
| 4a | BCP(B) + F(B) | 70/30 | 101.3 | 35.7 |
| 4b | BCP + F | — | 23.6 | 13.8 |
| 5a | 2:1CSD(B)BCP(B) + F(B) | 70/30 | 129.8 | 45.8 |
| 5b | 2:1CSD-BCP + F | — | 46.7 | 29.0 |
| 6a | 2:1CSD(B)BCP(B) + F(B) | 90/10 | 114.1 | 41.7 |
| 7a | 1:1CSD(B)BCP(B) + F(B) | 70/30 | 111.7 | 26.8 |
| 7b | 1:1CSD-BCP + F | — | 67.0 | 23.4 |
| 8a | 1:1CSD(B)BCP(B) + F(B) | 90/10 | 112.9 | 34.5 |
| | P value (ANOVA on RANKS) | | <0.001 | |

TABLE 24

Post Hoc test (comparison of BMP containing groups). All pairwise multiple comparison procedures (Student-Newman-Keuls Method):

| Comparison | Diff of Ranks | q | P < 0.05 |
|---|---|---|---|
| 3a-aBV vs 1a-aBV | 809.000 | 8.384 | Yes |
| 3a-aBV vs 4a-aBV | 569.000 | 6.734 | Yes |
| 3a-aBV vs 8a-aBV | 421.000 | 5.807 | Yes |
| 3a-aBV vs 7a-aBV | 408.000 | 6.744 | Yes |
| 3a-aBV vs 6a-aBV | 400.000 | 8.248 | Yes |
| 3a-aBV vs 2a-aBV | 386.000 | 10.576 | Yes |
| 3a-aBV vs 5a-aBV | 235.000 | 9.594 | Yes |
| 5a-aBV vs 1a-aBV | 574.000 | 6.793 | Yes |
| 5a-aBV vs 4a-aBV | 334.000 | 4.607 | Yes |
| 2a-aBV vs 1a-aBV | 423.000 | 5.835 | Yes |
| 4a-aBV vs 1a-aBV | 240.000 | 9.798 | Yes |
| 6a-aBV vs 1a-aBV | 409.000 | 6.761 | Yes |
| 7a-aBV vs 1a-aBV | 401.000 | 8.268 | Yes |
| 8a-aBV vs 1a-aBV | 388.000 | 10.631 | Yes |

Histological evaluation indicated that for all bioimplants the ossicles primarily comprised a shell of bone surrounding a mixture of bone, cartilage and marrow tissue. There were no signs of inflammation in any of the implants.

Figure 10A:
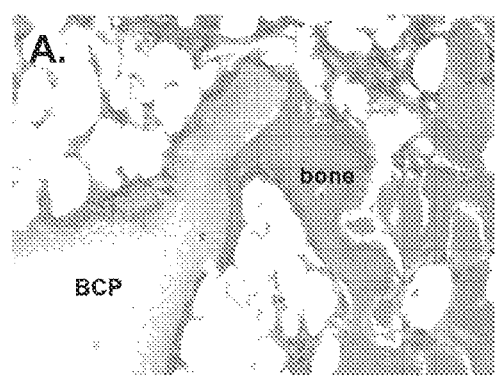
FIGS. 10A and 10B illustrate histological appearance of new bone formed around calcium phosphate (FIG. 10A) and calcium sulphate (FIG. 10B) carrier components used in a bioimplant produced according to the method of the invention.
Figure 10B:
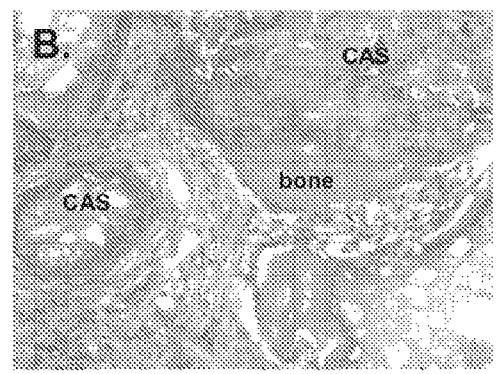

Residual calcium phosphate granules were visible in the Induce Bioimplants containing BCP, while calcium sulphate appears to be undergoing rapid resorption with only a few CAS granules seen. Bone was seen forming directly onto and into the CAS and BCP granules (FIG. 10A-B).

Discussion

Results from this study show that when BMP was distributed between being lyophilized onto carrier granules and mixed into the P407 gel, (a distribution which results in a multiphasic release of BMP) larger ossicles with more bone were produced than when all of the BMP was lyophilized onto the granules which were subsequently mixed with P407 gel at the time of surgery A 70/30 distribution between granules and P407 gel produced larger ossicles with more bone than a 90/10 distribution between granules and P407 gel.

In groups with an equal distribution of BMP between the granules and P407 CSD granules produced larger ossicles with more bone than similarly sized BCP granules, despite CSD-produced ossicles having a larger surface area due to being porous (BCP granules were solid). When CSD can be mixed with BCP bioimplants with 67% or more CSD granules produced larger ossicles than those with 50% or fewer CSD granules.

What is claimed is:

1. A system for multiphasic release of growth factors at a treatment site, the system comprising:
 a) a delivery vehicle comprising a polymer comprising poloxamer 407 and at least one first growth factor, wherein the delivery vehicle is adapted to release the at least one first growth factor in an initial release profile over a first time period; and
 b) a carrier comprising a plurality of particles having at least one second growth factor on the surfaces thereof, the carrier being adapted to release the at least one second growth factor over a second time period, wherein the second time period is of a longer duration than the first time period, and wherein the carrier comprises calcium sulphate dihydrate particles.

2. The system according to claim 1, wherein the carrier further comprises calcium phosphate particles.

3. The system according to claim 1, wherein the delivery vehicle is in the form of a liquid or a gel.

4. The system according to claim 1, wherein the particles of the carrier are dispersed within the delivery vehicle.

5. The system according to claim 1, wherein the first time period comprises hours or days.

6. The system according to claim 1, wherein the second time period comprises days or weeks.

7. The system according to claim 1, wherein the delivery vehicle is adapted to release at least 80% of the at least one first growth factor within a period of 72 hours.

8. The system according to claim 1, wherein the carrier releases the at least one second growth factor in a sustained release profile over the second time period.

9. The system according to claim 1, wherein the at least one first growth factor and the at least one second growth factor are the same.

10. The system according to claim 9, wherein the growth factor is bone morphogenetic protein 2 (BMP-2).

11. The system according to claim 10, wherein the delivery vehicle is adapted to release at least 10% of the total amount of the growth factor during the first time period and the carrier is adapted to release at least 50% of the total amount of the growth factor during the second time period.

12. The system according to claim 1, wherein the delivery vehicle to carrier ratio is from 0.5:1 to 4:1 (v/v).

13. The system according to claim 1, wherein the at least one second growth factor is applied as a solution to the carrier and then lyophilized onto the carrier.

14. The system according to claim 13, wherein the concentration of the at least one second growth factor in the solution is from 0.5 mg/ml to 2 mg/ml.

* * * * *